United States Patent
Hourtash et al.

(10) Patent No.: US 9,345,544 B2
(45) Date of Patent: May 24, 2016

(54) SYSTEMS AND METHODS FOR AVOIDING COLLISIONS BETWEEN MANIPULATOR ARMS USING A NULL-SPACE

(71) Applicant: Intuitive Surgical Operations, Inc., Sunnyvale, CA (US)

(72) Inventors: Arjang M. Hourtash, Santa Clara, CA (US); Pushkar Hingwe, Fremont, CA (US); Bruce Michael Schena, Menlo Park, CA (US); Roman L. Devengenzo, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 201 days.

(21) Appl. No.: 13/906,819

(22) Filed: May 31, 2013

(65) Prior Publication Data

US 2013/0325030 A1   Dec. 5, 2013

Related U.S. Application Data

(60) Provisional application No. 61/654,773, filed on Jun. 1, 2012.

(51) Int. Cl.
*A61B 19/00* (2006.01)
*B25J 9/16* (2006.01)

(52) U.S. Cl.
CPC ............ *A61B 19/2203* (2013.01); *B25J 9/1607* (2013.01); *B25J 9/1676* (2013.01);
(Continued)

(58) Field of Classification Search
CPC .................. A61B 19/2203; A61B 2019/2223; B25J 9/1607; B25J 9/1676; G05B 2219/39091; G05B 2219/40492; G05B 2219/40362; G05B 2219/39135; G05B 2219/40371; G05B 2219/40202; G05B 2219/40476; G05B 2219/45117
See application file for complete search history.

(56) References Cited

U.S. PATENT DOCUMENTS 3,920,972 A   11/1975   Corwin, Jr. et al.
4,028,533 A    6/1977   Matsubara
(Continued)

FOREIGN PATENT DOCUMENTS

EP   1234641 A1   8/2002
EP   1951139 A2   8/2008
(Continued)

OTHER PUBLICATIONS

Arthur Komainda and Manfred Hiller, Control of Heavy Load Manipulators in Varying Environments, Automatic and Robotics in Construction, 1999.*
(Continued)

*Primary Examiner* — Khoi Tran
*Assistant Examiner* — Abby Lin

(57) ABSTRACT

Devices, systems, and methods for avoiding collisions between manipulator arms using a null-space are provided. In one aspect, the system calculates an avoidance movement using a relationship between reference geometries of the multiple manipulators to maintain separation between reference geometries. In certain embodiments, the system determines a relative state between adjacent reference geometries, determines an avoidance vector between reference geometries, and calculates an avoidance movement of one or more manipulators within a null-space of the Jacobian based on the relative state and avoidance vector. The joints may be driven according to the calculated avoidance movement while maintaining a desired state of the end effector or a remote center location about which an instrument shaft pivots and may be concurrently driven according to an end effector displacing movement within a null-perpendicular-space of the Jacobian so as to effect a desired movement of the end effector or remote center.

66 Claims, 18 Drawing Sheets

(52) U.S. Cl.
CPC .................. *A61B2019/2223* (2013.01); *G05B 2219/39091* (2013.01); *G05B 2219/39135* (2013.01); *G05B 2219/40202* (2013.01); *G05B 2219/40362* (2013.01); *G05B 2219/40371* (2013.01); *G05B 2219/40476* (2013.01); *G05B 2219/40492* (2013.01); *G05B 2219/45117* (2013.01)

(56) References Cited

U.S. PATENT DOCUMENTS

| | | | |
|---|---|---|---|
| 4,063,073 | A | 12/1977 | Strayer |
| 4,578,757 | A | 3/1986 | Stark |
| 4,999,553 | A | 3/1991 | Seraji |
| 5,086,401 | A | 2/1992 | Glassman et al. |
| 5,130,632 | A | 7/1992 | Ezawa et al. |
| 5,159,249 | A | 10/1992 | Megherbi |
| 5,430,543 | A | 7/1995 | Howard |
| 5,513,100 | A | 4/1996 | Parker et al. |
| 5,550,953 | A | 8/1996 | Seraji |
| 5,587,937 | A | 12/1996 | Massie et al. |
| 5,632,758 | A | 5/1997 | Sklar |
| 5,710,870 | A | 1/1998 | Ohm et al. |
| 5,737,500 | A | 4/1998 | Seraji et al. |
| 5,823,980 | A | 10/1998 | Kopfer |
| 5,855,583 | A | 1/1999 | Wang et al. |
| 5,908,458 | A | 6/1999 | Rowe et al. |
| 6,037,927 | A | 3/2000 | Rosenberg |
| 6,098,260 | A | 8/2000 | Sarh |
| 6,246,200 | B1 | 6/2001 | Blumenkranz et al. |
| 6,312,435 | B1 | 11/2001 | Wallace et al. |
| 6,317,651 | B1 | 11/2001 | Gerstenberger et al. |
| 6,331,181 | B1 | 12/2001 | Tierney et al. |
| 6,377,011 | B1 | 4/2002 | Ben-Ur |
| 6,379,073 | B1 | 4/2002 | Yoo et al. |
| 6,400,115 | B1 | 6/2002 | Yamazoe |
| 6,424,885 | B1 | 7/2002 | Niemeyer et al. |
| 6,459,926 | B1 | 10/2002 | Nowlin et al. |
| 6,468,265 | B1 | 10/2002 | Evans et al. |
| 6,493,608 | B1 | 12/2002 | Niemeyer |
| 6,645,196 | B1 | 11/2003 | Nixon et al. |
| 6,678,582 | B2 | 1/2004 | Waled |
| 6,699,177 | B1 | 3/2004 | Wang et al. |
| 6,763,286 | B2 | 7/2004 | Metelski |
| 6,786,896 | B1 | 9/2004 | Madhani et al. |
| 7,083,571 | B2 | 8/2006 | Wang et al. |
| 7,280,633 | B2 | 10/2007 | Cheng et al. |
| 7,379,533 | B2 | 5/2008 | Koertge |
| 7,428,296 | B2 | 9/2008 | Bernhardt et al. |
| 7,564,949 | B2 | 7/2009 | Sattler et al. |
| 7,763,015 | B2 | 7/2010 | Cooper et al. |
| 8,004,229 | B2 | 8/2011 | Nowlin et al. |
| 8,041,459 | B2 | 10/2011 | Sutherland et al. |
| 8,123,740 | B2 | 2/2012 | Madhani et al. |
| 8,162,926 | B2 | 4/2012 | Schena |
| 2001/0013764 | A1 | 8/2001 | Blumenkranz et al. |
| 2001/0018591 | A1 | 8/2001 | Brock et al. |
| 2002/0082612 | A1 | 6/2002 | Moll et al. |
| 2002/0111713 | A1 | 8/2002 | Wang et al. |
| 2002/0120363 | A1 | 8/2002 | Salisbury et al. |
| 2003/0018412 | A1 | 1/2003 | Kimura et al. |
| 2003/0060927 | A1 | 3/2003 | Gerbi et al. |
| 2003/0065311 | A1 | 4/2003 | Wang et al. |
| 2003/0109780 | A1 | 6/2003 | Coste-Maniere et al. |
| 2003/0139753 | A1 | 7/2003 | Wang et al. |
| 2003/0216715 | A1 | 11/2003 | Moll et al. |
| 2004/0034283 | A1 | 2/2004 | Quaid, III |
| 2004/0039485 | A1 | 2/2004 | Niemeyer et al. |
| 2004/0042583 | A1 | 3/2004 | Wackerle et al. |
| 2004/0111183 | A1 | 6/2004 | Sutherland et al. |
| 2004/0186484 | A1 | 9/2004 | Ryan |
| 2005/0104549 | A1 | 5/2005 | Nishimura et al. |
| 2008/0037712 | A1 | 2/2008 | Klingenbeck-Regn |
| 2009/0234444 | A1 | 9/2009 | Maschke |
| 2009/0297011 | A1 | 12/2009 | Brunner et al. |
| 2010/0191371 | A1 | 7/2010 | Hornung et al. |
| 2011/0040306 | A1 | 2/2011 | Prisco et al. |
| 2011/0066282 | A1* | 3/2011 | Bosscher et al. ............... 700/248 |
| 2011/0172819 | A1* | 7/2011 | Lee et al. ....................... 700/253 |
| 2011/0218679 | A1 | 9/2011 | Cheng et al. |
| 2011/0264108 | A1 | 10/2011 | Nowlin et al. |
| 2011/0264109 | A1 | 10/2011 | Nowlin et al. |
| 2011/0264110 | A1 | 10/2011 | Nowlin et al. |
| 2011/0264111 | A1 | 10/2011 | Nowlin et al. |
| 2011/0264112 | A1 | 10/2011 | Nowlin et al. |
| 2011/0270271 | A1 | 11/2011 | Nowlin et al. |
| 2011/0276059 | A1 | 11/2011 | Nowlin et al. |

FOREIGN PATENT DOCUMENTS

| | | |
|---|---|---|
| EP | 1972415 A1 | 9/2008 |
| GB | 2311149 A | 9/1997 |
| JP | 2003159674 A | 6/2003 |
| WO | 9729690 | 8/1997 |
| WO | 9950721 A1 | 10/1999 |
| WO | 02051329 A1 | 7/2002 |
| WO | 02060653 A9 | 12/2002 |
| WO | WO-2007076119 A2 | 7/2007 |
| WO | 2008015666 A2 | 2/2008 |
| WO | WO-2013078529 A1 | 6/2013 |

OTHER PUBLICATIONS

Neville Hogan, Impedance Contro: An Approach to Manipulation, Journal of Dynamic Systems, Measurement, and Control, Mar. 1985.*

Albu-Schaffer A., et al., "Cartesian Impedance Control Techniques for Torque Controlled Light-Weight Robots," Proceedings of the 2002 IEEE, International Conference on Robotics and Automation, 2002, pp. 657-663.

Albu-Schaffer A., et al., "Parameter Identification and Passivity Based Joint Control for a 7DOF Torque Controlled Light Weight Robot," Proceedings of the 2001 IEEE, International Conference on Robotics and Automation, 2001, vol. 3, pp. 2852-2858.

Baerlocher, P. et al., "Task Priority Formulations for the Kinematic Control of Highly Redundant Articulated Structures," IEEE/RSJ International Conference on Intelligent Robots and Systems, 1998, pp. 323-329, vol. 1, IEEE.

Boyd, Stephen, "Convex Optimization," 2004, 8 pages, Cambridge University Press.

Da Vinci, Chirurgie-System Benutzerhandbuch, Intuitive Surgical Inc., 2004, 9 Chapters and 2 Appendixes, 260 pages.

English, James D. et al., "On the Implementation of Velocity Control for Kinematically Redundant Manipulators," IEEE transactions on systems, man, and cybernetics. Part A, Systems and humans, 2000, pp. 233-237, vol. 30—No. 3, IEEE.

Espiau, Bernard et al., "Collision Avoidance for Redundant Robots with Proximity Sensors," The Third International Symposium of Robotics Research, 1986, pp. 243-251, MIT Press.

European Search Report for Application No. EP10196665.3, mailed on Oct. 15, 2012, 8 pages. (017516-009802/EP).

European Search Report for Application No. EP10196666, mailed on Jul. 19, 2012, 7 pages (017516-009803/EP).

European Search Report for Application No. EP10196670.3 , mailed Oct. 26, 2012, 9 pages (017516-009806/EP).

European Search Report for Application No. EP10196671, mailed on Oct. 15, 2012, 7 pages (017516-009807/EP).

Extended EP Search Report and Written Opinion for Application No. EP10196669.5, mailed Jul. 26, 2012, 7 pages (017516-009805/EP).

Extended European Search Report and Written Opinion for Application No. EP10196664.6, mailed on Jul. 25, 2012, 7 pages (017516-009801/EP).

Extended European Search Report for Application No. EP101996666.1, mailed on Jul. 19, 2012, 7 pages. (017516-009803/EP).

Grunwald G., et al., "Programming by Touch: The Different Way of Human—Robot Interaction," IEEE Transactions on Industrial Electronics, 2003, vol. 50 (4), pp. 659-666.

(56) References Cited

OTHER PUBLICATIONS

Hirzinger G., et al., "A Mechatronics Approach to the Design of Light-Weight Arms and Multifingered Hands," Proceedings of the 2000 IEEE, International Conference on Robotics and Automation, 2000, pp. 46-54.
Hirzinger G., et al., "On a New Generation of Torque Controlled Light-Weight Robots," Proceedings of the 2001 IEEE, International Conference on Robotics and Automation, 2001, pp. 3356-3363.
Howe R.D., et al., "Robotics for Surgery," Annual Review of Biomedical Engineering, 1999, vol. 1, pp. 211-240.
Interlink Electronics, "Force Sensing Resistors for Medical Equipment, Automotive, and Musical Instruments," 2003, 1 page, Internet: http://www.interlinkelec.com/products/fsr/fsr.htm (last visited Jul. 2003).
International Search Report and Written Opinion for Application No. PCT/US2006/017843, mailed on Jan. 4, 2007, 11 pages (017516-009800/PCT).
International Search Report and Written Opinion for Application No. PCT/US2013/043557, mailed on Sep. 6, 2013, 15 pages.
International Search Report and Written Opinion for Application No. PCT/US2013/043564, mailed on Sep. 6, 2013, 16 pages.
International Search Report and Written Opinion for Application No. PCT/US2013/043578, mailed on Sep. 5, 2013, 14 pages.
Kazanzides, Peter et al., "Force Sensing and Control for a Surgical Robot," Int. Conference on Robotics and Automation, May 1992, Nice, France; pp. 612-617, vol. 1, IEEE.
Khatib O., "A Unified Approach for Motion and Force Control of Robot Manipulators: The Operational Space Formulation," IEEE Journa of Robotics and Automation, 1987, vol. RA-3 (1), pp. 43-52.
Konietschke R., et al., "A Preoperative Planning Procedure for Robotically Assisted Minimally Invasive Interventions," Lecture Notes in Computer Science, CURAC, 2004.
Konietschke R., et al., "Manipulability and Accuracy Measures for a Medical Robot in Minimally Invasive Surgery," Conference Proceeding, In proceeding of: 9th International Symposium on Advances in Robot Kinematics(ARK), Sestri Levante, Italy, Jun. 28-Jul. 1, 2004, 8 pages.
Krupa A., et al., "Towards Semi-Autonomy in Laparoscopic Surgery Through Vision and Force Feedback Control," Experimental Robotics VII, Lecture Notes in Control and Information Sciences, 2001, vol. 271, pp. 189-198.
Maciejewski A.A., et al., "Obstacle Avoidance for Kinematically Redundant Manipulators in Dynamically Varying Environments," International Journal of Robotics Research, 1985, vol. 4 (3), pp. 109-117.
Maciejewski, Anthony A. et al., "The Singular Value Decomposition: Computation and Applications to Robotics," The International Journal of Robotics Research, 1989, pp. 63-79, vol. 8—No. 6, SAGE Publications.
Michelin M., et al., "Dynamic Task/Posture Decoupling for Minimally Invasive Surgery Motions," Intelligent Robots and Systems, 2004, vol. 4, pp. 3625-3630.
Monnich, Holger et al., "OP:Sense; Research platform for semi-autonomous robot-assisted surgery with haptic feedback and optical supervision" [online video], 2011 [retrieved on Jun. 12, 2013]. Retrieved from the Internet: <URL: https://www.youtube.com/watch?v=g0ZgSaNtTUw.
Nakamura Y., et al., "Task-Priority Based Redundancy Control of Robot Manipulators," International Journal of Robotics Research, Sage Science Press, Thousand Oaks, US, Jun. 21, 1987, vol. 6 (2), pp. 3-15.
Ortmaier T.J., "Motion Compensation in Minimally Invasive Robotic Surgery," 2002, 5 Chapters, 147 pages.
PCT/US06/17843 International Search Report, mailed Jan. 4, 2007, 6 pages.
PCT/US06/17843 Written Opinion of the International Search Authority, mailed Jan. 4, 2007, 9 pages.
Schreiber G., "Interactive Redundant Robotics: Control of the Inverted Pendulum with Nullspace Motion," Proceedings of the 2001, IEEE/RSJ, International Conference on Intelligent Robots and Systems, 2001, pp. 158-164.
Schreiber G., Steuerung fur Redundante Robotersysteme: Benutzer und Aufgabenorientierte Verwendung Der Redundanz, 2004, 296 pages.
Siciliano B., "Kinematic Control of Redundant Robot Manipulators: A Tutorial," Journal of Intelligent and Robotic Systems, 1990, vol. 3 (3), pp. 201-212.
Siciliano, Bruno et al., "A General Framework for Managing Multiple Tasks in Highly Redundant Robotic Systems," Fifth International Conference of Advanced Robotics, 1991, pp. 1211-1216, IEEE.
Smalley, Eric, "Flexible sensors make robot skin," Technology Research News, Sep. 22/29, 2004, 3 pages, Internet: http://www.trnmag.com/Stories/2004/092204/Flexible_sensors_make_robot_skin%20_092204.html (last visited Dec. 17, 2004).
Stanford University, Dexterous Manipulation Laboratory, "The 'Capaciflector' Proximity Sensor", 2005, 3 pages. Internet: http://www.cdr.stanford.edu/Touch/previous_projects/capaciflector/capaciflector.htm (last visited Jan. 5, 2005).
Tapeswitch Corporation, Data Sheet for Controflex Ribbon Switches, last downloaded Dec. 17, 2004, 2 pages, Internet: http://www.tapeswitch.com/nroducts/contflex,php.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Yigit S., et al., "Specific Combined Control Mechanisms for Human Robot Co-Operation," Institute for Process Control and Robotics (IPR), 2003, 6 pages.
European Application Serial No. 13796776.6, Extended European Search Report mailed Jan. 19, 2016, 11 pgs.
Fratu, A, et al., "Using the Redundant Inverse Kinematics System for Collision Avoidance", 2010 3rd International Symposium on Electrical and Electronics Engineering (ISEEE), (2010), 88-93.

\* cited by examiner

SYSTEMS AND METHODS FOR AVOIDING COLLISIONS BETWEEN MANIPULATOR ARMS USING A NULL-SPACE

CROSS-REFERENCES TO RELATED APPLICATIONS

This application is a Non-Provisional of and claims the benefit of priority from U.S. Provisional Patent Application No. 61/654,773 filed on Jun. 1, 2012 and entitled "Systems and Methods for Avoiding Collisions Between Manipulator Arms Using a Null-Space", the full disclosure of which is incorporated herein by reference.

The present application is generally related to the following commonly-owned applications: U.S. application Ser. No. 12/494,695 filed Jun. 30, 2009, entitled "Control of Medical Robotic System Manipulator About Kinematic Singularities;" U.S. application Ser. No. 12/406,004 filed Mar. 17, 2009, entitled "Master Controller Having Redundant Degrees of Freedom and Added Forces to Create Internal Motion;" U.S. application Ser. No. 11/133,423 filed May 19, 2005 (U.S. Pat. No. 8,004,229), entitled "Software Center and Highly Configurable Robotic Systems for Surgery and Other Uses;" U.S. application Ser. No. 10/957,077 filed Sep. 30, 2004 (U.S. Pat. No. 7,594,912), entitled "Offset Remote Center Manipulator For Robotic Surgery;" U.S. patent application Ser. No. 09/929,453 filed on Aug. 13, 2001, (U.S. Pat. No. 7,048,745) entitled "Surgical Robotic Tools, Data Architecture, and Use;" U.S. application Ser. No. 09/398,507 filed Sep. 17, 1999 (U.S. Pat. No. 6,714,839), entitled "Master Having Redundant Degrees of Freedom;" and U.S. application Ser. No. 13/906,713 filed on May 31, 2013, entitled "Manipulator Arm-to-Patient Collision Avoidance Using a Null-Space;" and Ser. No. 13/906,767 filed on May 31, 2013, entitled "System and Methods for Commanded Reconfiguration of a Surgical Manipulator Using the Null-Space" filed concurrently with the present application; the disclosures of which are incorporated herein by reference in their entireties.

BACKGROUND OF THE INVENTION

The present invention generally provides improved surgical and/or robotic devices, systems, and methods.

Minimally invasive medical techniques are aimed at reducing the amount of tissue which is damaged during diagnostic or surgical procedures, thereby reducing patient recovery time, discomfort, and deleterious side effects. Millions of "open" or traditional surgeries are performed each year in the United States; many of these surgeries can potentially be performed in a minimally invasive manner. However, only a relatively small number of surgeries currently use minimally invasive techniques due to limitations in surgical instruments, techniques, and the additional surgical training required to master them.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments. The robotic surgical instruments can be inserted through small, minimally invasive surgical apertures to treat tissues at surgical sites within the patient, often the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

The servomechanism used for telesurgery will often accept input from two master controllers (one for each of the surgeon's hands) and may include two or more robotic arms or manipulators. Mapping of the hand movements to the image of the robotic instruments displayed by the image capture device can help provide the surgeon with accurate control over the instruments associated with each hand. In many surgical robotic systems, one or more additional robotic manipulator arms are included for moving an endoscope or other image capture device, additional surgical instruments, or the like.

A variety of structural arrangements can be used to support the surgical instrument at the surgical site during robotic surgery. The driven linkage or "slave" is often called a robotic surgical manipulator, and example linkage arrangements for use as a robotic surgical manipulator during minimally invasive robotic surgery are described in U.S. Pat. Nos. 6,758,843; 6,246,200; and 5,800,423, the full disclosures of which are incorporated herein by reference. These linkages often make use of a parallelogram arrangement to hold an instrument having a shaft. Such a manipulator structure can constrain movement of the instrument so that the instrument shaft pivots about a remote center of spherical rotation positioned in space along the length of the rigid shaft. By aligning this center of rotation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 6,702,805; 6,676,669; 5,855,583; 5,808,665; 5,445,166; and 5,184,601, the full disclosures of which are incorporated herein by reference.

While the new robotic surgical systems and devices have proven highly effective and advantageous, still further improvements would be desirable. For example, when moving the surgical instruments within a minimally invasive surgical site, robotic surgical manipulators may exhibit a significant amount of movement outside the patient, particularly when pivoting instruments about minimally invasive apertures through large angular ranges, which can lead to the moving manipulators inadvertently coming into contact with each other, with instrument carts or other structures in the surgical room, with surgical personnel, and/or with the outer surface of the patient. In particular, the volume of the manipulator arm may contact or collide with an adjacent manipulator arm, which may cause undesirable movement and/or stresses on the manipulator arms. Alternative manipulator structures have been proposed which employ software control over a highly configurable kinematic manipulator joint set to restrain pivotal motion to the insertion site while inhibiting inadvertent manipulator/manipulator contact outside the patient (or the like). These highly configurable "software center" surgical manipulator systems may provide significant advantages, but may also present challenges. In particular, the mechanically constrained remote-center linkages may have safety advantages in some conditions. Additionally, the wide range of configurations of the numerous joints often included in these manipulators may result in the manipulators being difficult to manually set-up in a configuration that is desirable for a particular procedure. Nonetheless, as the range of surgeries being performed using telesurgical systems continues to expand, there is an increasing demand for expanding the available configurations and the range of motion of the instruments within the patient. Unfortunately, both of these changes can increase the challenges associated with controlling and predicting the motion of the manipulators outside the body, and increase the importance of avoiding undesirable contact or collision between components of the manipulator arm and an adjacent manipulator arm.

For these and other reasons, it would be advantageous to provide improved devices, systems, and methods for surgery, robotic surgery, and other robotic applications. It would be particularly beneficial if these improved technologies provided the ability to avoid collisions between adjacent manipulator arms while maintaining a desired end effector state or a desired location of a remote center about which the instrument shaft pivots. Ideally, these improvements would allow for improved movement of one or more manipulator arms during a surgical procedure while avoiding collisions between the manipulator arms during end effector movement. Additionally, it would be desirable to provide such improvements while increasing the range of motion of the instruments for at least some procedures and without significantly increasing the size, mechanical complexity, or costs of these systems, and while maintaining or improving their dexterity.

BRIEF SUMMARY OF THE INVENTION

The present invention generally provides improved robotic and/or surgical devices, systems, and methods. In many embodiments, the invention will employ highly configurable surgical robotic manipulators. These manipulators, for example, may have more degrees of freedom of movement than the associated surgical end effectors have within a surgical workspace of a patient. A robotic surgical system in accordance with the present invention typically includes a manipulator arm supporting a robotic surgical instrument and a processor to calculate coordinated joint movements for manipulating an end effector of the instrument. The joints of the robotic manipulators supporting the end effectors allow the manipulator to move throughout a range of different configurations for a given end effector position and/or a given pivot point location. The system allows for movement of the highly configurable robotic manipulators to avoid collisions between manipulator arms by driving one or more joints of the manipulator according to coordinated movement of the joints calculated by a processor, which extends one or more joints of the manipulator within a null-space of the kinematic Jacobian so as to maintain the desired end effector state and/or pivot point location. In many embodiments, an avoidance movement is calculated in response to a determination that a distance between interacting elements or potentially colliding structures of adjacent manipulator arms is less than desired.

In one aspect, a redundant degrees of freedom (RDOF) surgical robotic system with manipulate input is provided. The RDOF surgical robotic system comprises a manipulator assembly, one or more user input devices, and a processor with a controller. A manipulator arm of the assembly has a plurality of joints providing sufficient degrees of freedom that allow a range of joint states for a given end effector state. In response to a determination that a portion of the manipulator arm proximal of the distal end effector is too close to a portion of an adjacent manipulator, the system calculates an avoidance movement of the plurality of joints of one or both manipulators within the null-space of their respective Jacobians. The processor is configured to then drive the joints, using a controller, according to the calculated avoidance movement so as to maintain a desired state of the end effector. Additionally, in response to receiving a manipulation command to move the end effector with a desired movement, the system calculates an end effector displacing movement of the joints by calculating joint movement along a null-perpendicular space of the Jacobian orthogonal to the null-space and drives the joints according to the calculated displacement movement to effect the desired end effector movement, often concurrently with driving the joints according to the calculated avoidance movement.

In another aspect of the present invention, the manipulator is configured to move such that an intermediate portion of the instrument shaft pivots about a remote center. Between the manipulator and the instrument, there are a plurality of driven joints providing sufficient degrees of freedom to allow a range of joint states for an end effector position as the intermediate portion of the instrument shaft extends through an access site. A processor having a controller couples an input device to the manipulator. In response to a determination that a portion of the manipulator arm is too close to a portion of an adjacent manipulator, the processor determines movements of one or more joints to increase the distance between the nearest portions of the manipulator arms while the intermediate portion of the instrument of each manipulator arm remains within the respective access site and the desired remote center location about which each instrument shaft pivots is maintained. Upon receiving a manipulation command to effect a desired movement of an end effector of one or more manipulators, the system calculates end effector displacing movement of the joints of the corresponding manipulator, which comprises calculating joint movement along a null-perpendicular space orthogonal to the null-space and then drives the joints of the respective manipulator according to the calculated movement to effect the desired end effector movement in which the instrument shaft pivots about the remote center, often concurrently with driving of the joints according to the calculated avoidance movement.

In another aspect, the system determines a reference geometry of a first manipulator and a reference geometry of a second manipulator, the reference geometries typically including multiple line segments corresponding to structures of each manipulator arm, and determines a relative state between the reference geometries. The system then determines an avoidance vector extending between portions of the first and second reference geometries that overlap (e.g. capable of colliding). The avoidance vector for the first manipulator points in the direction that tends to move the overlapping geometry of the first manipulator away from the second manipulator. The avoidance vector for the second manipulator points in the direction that tends to move the overlapping geometry of the second manipulator away from the first manipulator. The avoidance vector for the second manipulator, also points in the opposite direction as the avoidance vector for the first manipulator. In response to a determination that a separation between the reference geometries is less than desired, the system then determines a parameter associated with an avoidance vector, such as a virtual force or a commanded velocity, between the reference geometries sufficient to increase separation when applied along the avoidance vector. The parameters are typically calculated in a three-dimensional work space of the manipulator arms in which the corresponding reference geometries move and are then converted into a joint space of the joints. Alternatively, other methods of calculating an avoidance movement may be used, including those described below (e.g., based on null-space basis vectors or a potential field in joint space). Using the joint space, the system calculates the avoidance movement so as to increase the separation while extending the joints and links within a null-space of the Jacobian associated with the manipulator arm. By driving the joints according to the calculated avoidance movement, the system effects the avoidance movement so as to inhibit collisions between adjacent manipulator arms while maintaining a desired state of a distal portion (e.g. end effector) of the manipulator arms.

In one aspect, each reference geometry comprises multiple line segments, and determining a relative state comprises determining the nearest pair of line segments from adjacent reference geometries. Although the use of line segments to represent the manipulator arms is described throughout, it is appreciated that any suitable geometry could be used (e.g. points, line segment, spheres, a string of spheres, cylinders, volumes, or various geometric shapes). In another aspect, determining a nearest pair comprises determining a closest distance between points on the line segment pair. From the first and second reference geometries, the system may determine, in a three-dimensional work space of the manipulator arms, one or more pairs of interacting elements (e.g. line segments having ranges of motion in the work space that overlap) and then determine a relative state between the reference geometries and an avoidance vector extending between the reference geometries. The system then determines a movement of the reference geometries along the vector, often by simulating a force applied along the vector or a commanded velocity applied to a point on the line segment along the direction of the avoidance vector, which is then converted into the joint space. The movement along the joint space is then projected onto a null-space of the Jacobian so as to calculate the avoidance movement to maintain separation between the reference geometries while maintaining a desired state of a distal portion (e.g. end effector) of each of the first and second manipulator arms.

In certain embodiments, each of the first and second reference geometries may include one or more points, line segments, volumes or more sophisticated solid modeling corresponding to a component or volume of the manipulator arm. In some embodiments, each of the first and second reference geometries includes multiple line segments, each line segment corresponding to a link or protruding portion of a particular manipulator arm, and the relative state between the first and second reference geometries corresponds to a proximity between manipulator arms, such as a distance between positions or velocities of the first and second reference geometries. The proximity may be sensed locally by proximity sensors mounted to the driven linkages or "slaves." In response to a determination that the relative state is undesirable, such as a less than desired separation, the system calculates an avoidance movement of one or more joints of one or more of the manipulator arms within the null-space to increase the separation distance while maintaining the desired state of a distal portion (e.g. end effector) of each manipulator arm or position of a remote center associated with each manipulator arm.

In certain embodiments, in response to a determination that a shortest distance between the first and second reference geometry is less than desired, which may be a pre-determined distance or a function of joint states, a processor of the system calculates an avoidance movement of the joints or links of one or both manipulator arms within their associated null-space by driving the joints of the respective manipulator arm to increase the separation between the manipulator arms. The desired state of the end effector may include a desired position, velocity or acceleration of the end effector, or a pivotal motion about a remote center. The end effector manipulation command is received from an input device by a user, such as a surgeon entering the command on a surgical console master input, while the avoidance movement is calculated and used to drive the joints to provide sufficient clearance between the manipulator arms when the distance between reference geometries is less than desired. In some embodiments, the distal portion or end effector of each arm includes or is configured to releasably support a surgical instrument having an elongate shaft extending distally to a surgical end effector, wherein each instrument shaft pivots about a remote center during surgery, and wherein the avoidance movement of the one or more joints is calculated so as to maintain a position of the remote center during driving of the joints. In some embodiments, the joints of one or more manipulator arms include a revolute joint near a distal portion (e.g. end effector) of the manipulator arm that pivots the insertion axis about an axis of the distal revolute joint, the axis extending through the remote center. The end effector displacing movement may be calculated so that a first set of joints, often the distal revolute joint, is not driven such that the first set of joints is effectively locked out or the end effector displacing movement of the joints is calculated such that the first set of joints is not driven to effect the desired distal portion displacing movement (e.g. end effector displacing movement), while the avoidance movement of the joints may be calculated so as to drive at least the distal revolute joint of one or more manipulator arms. The first set of joints includes one or more joints of the manipulator arm.

In an example embodiment, each manipulator arm is configured to support a tool having an intermediate portion extending along an insertion axis distally of the proximal portion and an end effector at a distal end of each intermediate portion, wherein at least some of the joints mechanically constrain movement of the distal portion (e.g. end effector) relative to the base such that the distal portion of the respective manipulator arm pivots about a remote center disposed at the insertion axis to facilitate movement of the end effector at a work site, wherein the work site is accessed through an insertion opening. The plurality of joints of each manipulator arm may include remote spherical center joints disposed distally of the proximal portion and proximally of the distal portion of the respective manipulator arm, wherein the remote spherical center joints are mechanically constrained so that articulation of the remote spherical center joints pivot the distal portion of the respective manipulator arm about first, second, and third remote center axes, the first, second, and third remote center axes intersecting its remote center. In some embodiments, the avoidance movement is independent of a planar relationship between the manipulator arms when each arm is disposed in a substantially planar configuration, thereby allowing for an increased range of configuration for each arm while inhibiting collisions between the first and second manipulators where their respective ranges of motion overlap.

In certain embodiments, a first joint coupling the proximal portion of a manipulator arm to the proximal base is a revolute joint that supports the respective manipulator arm so that joint movement of the first joint pivots one or more joints of the manipulator arm about a pivotal axis of the revolute joint. In some embodiments, the pivotal axis of the revolute joint extends from the joints through the end effector, preferably through a remote center about which an instrument shaft of the end effector pivots. In one aspect, movement of the revolute joint pivots one or more joints of the manipulator arm about a cone distally tapered and oriented towards the distal end effector or remote center. The cone around which the manipulator arm pivots in this aspect, corresponds to a cone shaped void within the range of motion of the tool tip, in which the movement of the tool may be impossible or impaired. In another aspect, the joint coupling the proximal portion of the manipulator to the base is moveable relative to the base along a path, typically an arcuate or substantially circular path such that movement of the joint along the path pivots one or more joints of the manipulator arm about an axis extending through a remote center about which the instrument shaft pivots. The first joint may be driven so as to pivot about its revolute axis and/or move along its path in response to an input from a user to drive the joint and reconfigure the respective manipulator arm within a null-space of the Jacobian as desired.

In yet another aspect of the present invention, a surgical robotic manipulator with a proximal revolute joint and a distal parallelogram linkage is provided, the pivotal axis of the revolute joint substantially intersecting with the axis of the instrument shaft of the end effector, preferably at a remote center if applicable. The system further includes a processor having a controller coupling the input to the manipulator arm and configured to calculate the avoidance movement of the plurality of joints as in any of the embodiments described herein. The above described aspect of calculating the avoidance movement to drive a particular joint that is not driven in the calculated displacement movement or vice versa may be applied to any of the joints of the manipulator arm described herein.

A further understanding of the nature and advantages of the present invention will become apparent by reference to the remaining portions of the specification and drawings.

DETAILED DESCRIPTION OF THE INVENTION

Figure 1A:
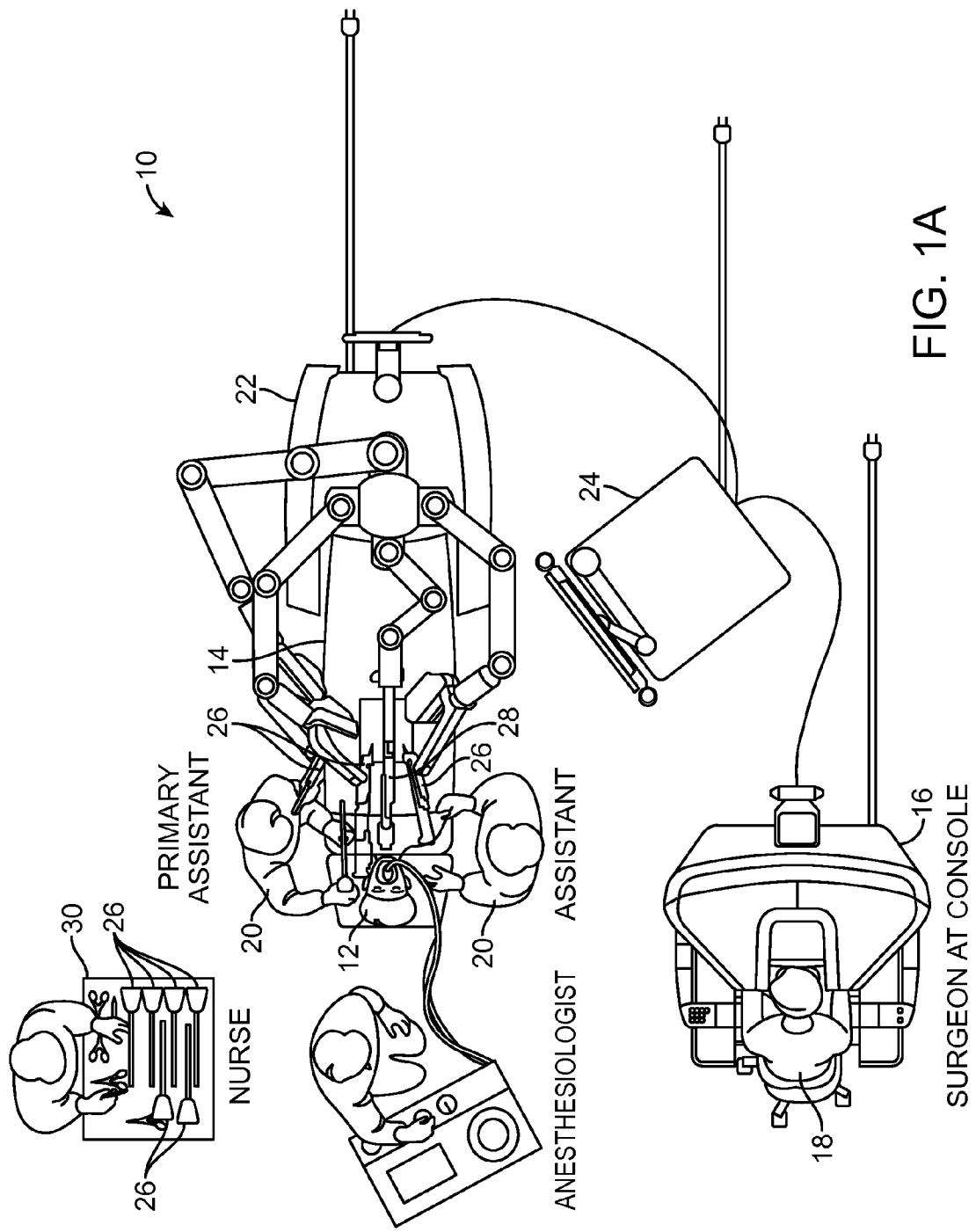
FIG. 1A is an overhead view of a robotic surgical system in accordance with embodiments of the present invention, the robotic surgical system having a surgical station with a plurality of robotic manipulators for robotically moving surgical instruments having surgical end effectors at an internal surgical site within a patient.

The present invention generally provides improved surgical and robotic devices, systems, and methods. The invention is particularly advantageous for use with surgical robotic systems in which a plurality of surgical tools or instruments will be mounted on and moved by an associated plurality of robotic manipulators during a surgical procedure. The robotic systems will often comprise telerobotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site. The large number of degrees of freedom allow for movement or reconfiguration of the linkages of the manipulator assemblies within a null-space of the Jacobian so as to move the linkages of a first manipulator away from one or more adjacent manipulators while maintaining the desired end effector state. In certain embodiments, the system determines when a distance between a portion of the manipulator arm and one or more adjacent manipulator arms is less than desired and then drives the joints according to a calculated avoidance movement that extends or moves the joints of one or more manipulator arms within their respective null-space so as to increase the distance between the portion of the manipulator arm and the one or more adjacent manipulator arms. Often, the joints of the manipulator arm are driven according to the calculated avoidance movement concurrently with commanded displacement movement of a distal end effector during a surgical procedure.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector that is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base which is fixed in space during at least a portion of a robotic procedure and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both. When used for minimally invasive robotic surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site into a surgical workspace, rotation of the shaft about its axis, and pivotal motion of the shaft about a pivot point adjacent the access site.

Many of the example manipulator assemblies described herein have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation-plus three degrees of freedom to comply with the access site constraints), but may have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly within the null-space.

The invention provides robotic linkage structures which are particularly well suited for surgical (and other) applications in which a wide range of motion is desired, and for which a limited dedicated volume is available due to the presence of other robotic linkages, surgical personnel and equipment, and the like. The large range of motion and reduced volume needed for each robotic linkage may also provide greater flexibility between the location of the robotic support structure and the surgical or other workspace, thereby facilitating and speeding up setup.

The term "state" of a joint or the like will often herein refer to the control variables associated with the joint. For example, the state of an angular joint can refer to the angle defined by that joint within its range of motion, and/or to the angular velocity of the joint. Similarly, the state of an axial or prismatic joint may refer to the joint's axial position, and/or to its axial velocity. While many of the controllers described herein comprise velocity controllers, they often also have some position control aspects. Alternative embodiments may rely primarily or entirely on position controllers, acceleration controllers, or the like. Many aspects of control system that can be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control algorithm, a velocity control algorithm, a combination of both, and/or the like.

In certain embodiments, the tool of an example manipulator arm pivots about a pivot point adjacent a minimally invasive aperture. The system may utilize a hardware remote center, such as the remote center kinematics described in U.S. Pat. No. 6,786,896, the contents of which are incorporated herein in its entirety. Such systems may utilize a double parallelogram linkage which constrains movement of the linkages such that the shaft of the instrument supported by the manipulator pivots about a remote center point. Alternative mechanically constrained remote center linkage systems are known and/or may be developed in the future. Surprisingly, work in connection with the present invention indicates that remote center linkage systems may benefit from highly configurable kinematic architectures. In particular, when a surgical robotic system has a linkage that allows pivotal motion about two axes intersecting at or near a minimally invasive surgical access site, the spherical pivotal motion may encompass the full extent of a desired range of motion within the patient, but may still suffer from avoidable deficiencies (such as being poorly conditioned, being susceptible to arm-to-arm or arm-to-patient contact outside the patient, and/or the like). At first, adding one or more additional degrees of freedom that are also mechanically constrained to pivotal motion at or near the access site may appear to offer few or any improvements in the range of motion. Nonetheless, such joints can provide significant advantages by allowing the overall system to be configured in or driven toward a collision-inhibiting pose by further extending the range of motion for other surgical procedures, and the like.

In other embodiments, the system may utilize software to achieve a remote center, such as described in U.S. Pat. No. 8,004,229, the entire contents of which are incorporated herein by reference. In a system having a software remote center, the processor calculates movement of the joints so as to pivot an intermediate portion of the instrument shaft about a calculated pivot point location, as opposed to a pivot point determined by a mechanical constraint. By having the capability to compute software pivot points, different modes characterized by the compliance or stiffness of the system can be selectively implemented. More particularly, different system modes over a range of pivot points/centers (e.g., moveable pivot points, passive pivot points, fixed/rigid pivot point, soft pivot points) can be implemented as desired; thus, embodiments of the present invention are suitable for use in various types of manipulator arms, including both software center arms and hardware center arms.

Despite the many advantages of a robotic surgical system having multiple highly configurable manipulators, since the manipulators include a relatively large number of joints and links between the base and instrument, movement of the manipulator arms can be particularly complex. As the range of configurations and range of motion of the manipulator arm increases so does the likelihood of arm-to-arm collisions between a portion of the manipulator arm proximal of the distal end effector and an adjacent manipulator. For example, the considerable range of motion of a manipulator arm having a distal tool that pivots about a remote center adjacent a minimally invasive aperture, as described herein, can allow a protruding portion of the manipulator arm or a distal link of the manipulator arm itself to contact and/or collide with an link or protruding portion of an adjacent manipulator. Since the precise movement of the plurality of joints of a manipulator arm is particularly complex, arm-to-arm collisions can be a recurring problem and can be difficult to avoid. The present invention avoids such arm-to-aim collisions by calculating an avoidance movement of the manipulator arm within a null-space of the Jacobian and driving the joints to effect the avoidance movement while maintaining the desired state of a distal portion or tool of the manipulator arm, thereby avoiding collisions between multiple manipulator arms while effecting a desired end effector movement.

Embodiments of the invention include a processor that calculates an avoidance movement which facilitates use of driven joints of the kinematic linkage to reconfigure the manipulator structure within a null-space to avoid arm-to-arm collisions, in response to a determination that a distance between a first reference geometry and a second reference geometry is less than desired, the first reference geometry corresponding to one or more parts of a first manipulator arm and the second reference geometry corresponding to one or more part of a second adjacent manipulator arms. In other, embodiments, the system includes additional manipulator arms each having a corresponding reference geometry, such as a third manipulator arm having a third reference geometry and a further manipulator arm having a fourth reference geometry. In such embodiments, the system may further determine a relative state between each of the reference geometries and an avoidance vector extending therebetween, such as, between each nearest points on one or more pairs of reference geometries or line segments, and calculate the avoidance movement of one or more of the manipulator arms so as to maintain a sufficient distance between each of the adjacent reference geometries.

In certain embodiments, the system uses a defined reference geometry which corresponds to a portion of the manipulator having a range of motion that overlaps with an adjacent manipulator such that the portion is susceptible to a collision with the adjacent manipulators when each moves into the region of overlap within its respective range of motion. The first reference geometry may be a single point, or more typically multiple line segments that corresponds to linkages and/or protruding portions of the manipulator arm. The system then determines a relative state between the defined reference geometries of adjacent arms, of which the state may be any of a position, velocity or acceleration of the reference geometry. The relative state may be a distance between or may include a difference between the velocity vectors of each reference geometry. In some embodiments, the avoidance movement is calculated using this relative state and combined with a calculated movement to effect a desired displacing movement commanded by a user. In such an embodiment, the avoidance movement may be minimal or negligible if the relative state indicates that a collision is unlikely and the avoidance movement may be substantially greater when the relative state is indicative of an imminent collision.

In certain embodiments, the state of each reference geometry is determined using joint sensors in the respective manipulator arm to allow comparison between the reference geometry states so as to allow the processor to determine the relative joint state for use in calculating the avoidance movement. A controller of the surgical system may include a processor with a readable memory having joint controller programming instructions or code recorded thereon that allows the processor to derive suitable joint commands for driving the joints to allow the controller to effect movement of the joints of a manipulator to avoid collisions with an adjacent manipulator and/or to effect the desired end effector movement.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Referring now to the drawings, in which like reference numerals represent like parts throughout the several views, FIG. 1A is an overhead view illustration of a Minimally Invasive Robotic Surgical (MIRS) system 10, in accordance with some embodiments, for use in performing a minimally invasive diagnostic or surgical procedure on a Patient 12 who is lying down on an Operating table 14. The system can include a Surgeon's Console 16 for use by a surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the surgeon 18 views the surgical site through the Console 16. An image of the surgical site can be obtained by an endoscope 28, such as a stereoscopic endoscope, which can be manipulated by the Patient Side Cart 22 so as to orient the endoscope 28. The Electronics Cart 24 can be used to process the images of the surgical site for subsequent display to the surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 1B:
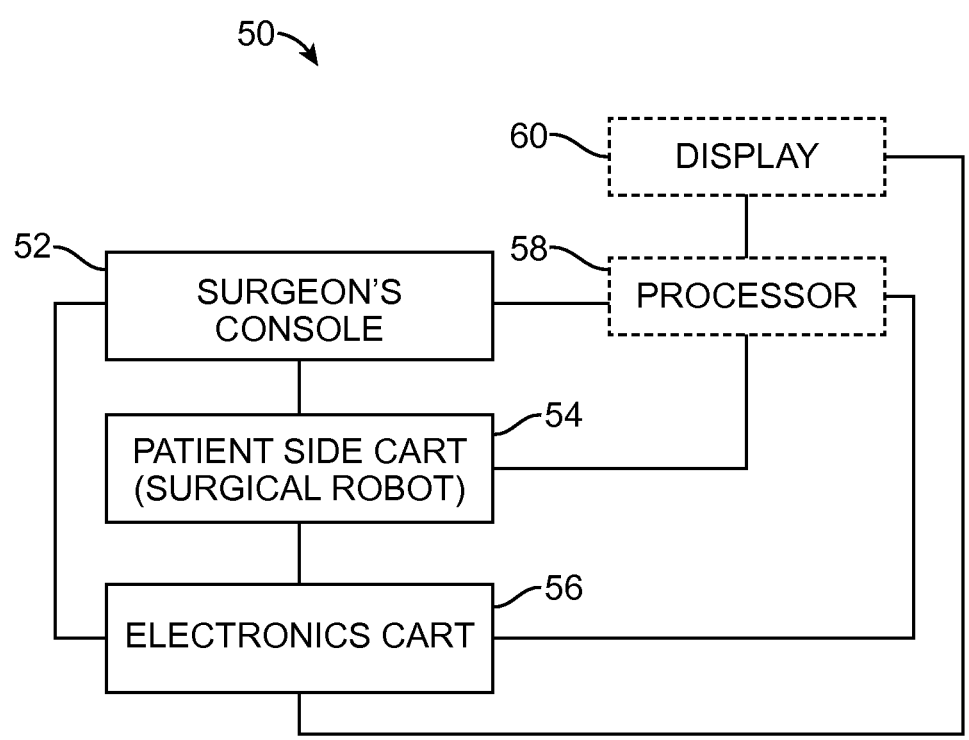
FIG. 1B diagrammatically illustrates the robotic surgical system of FIG. 1A.

FIG. 1B diagrammatically illustrates a robotic surgery system 50 (such as MIRS system 10 of FIG. 1A). As discussed above, a Surgeon's Console 52 (such as Surgeon's Console 16 in FIG. 1A) can be used by a surgeon to control a Patient Side Cart (Surgical Robot) 54 (such as Patent Side Cart 22 in FIG. 1A) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1A). As discussed above, the Electronics Cart 56 can process the captured images in a variety of ways prior to any subsequent display. For example, the Electronics Cart 56 can overlay the captured images with a virtual control interface prior to displaying the combined images to the surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 2:
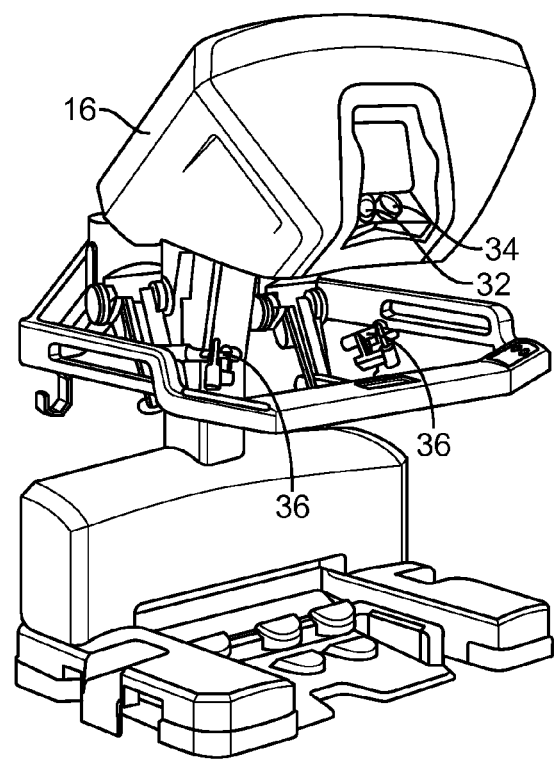
FIG. 2 is a perspective view illustrating a master surgeon console or workstation for inputting surgical procedure commands in the surgical system of FIG. 1A, the console including a processor for generating manipulator command signals in response to the input commands.

FIG. 2 is a perspective view of the Surgeon's Console 16. The Surgeon's Console 16 includes a left eye display 32 and a right eye display 34 for presenting the surgeon 18 with a coordinated stereo view of the surgical site that enables depth perception. The Console 16 further includes one or more input control devices 36, which in turn cause the Patient Side Cart 22 (shown in FIG. 1A) to manipulate one or more tools. The input control devices 36 can provide the same degrees of freedom as their associated tools 26 (shown in FIG. 1A) so as to provide the surgeon with telepresence, or the perception that the input control devices 36 are integral with the tools 26 so that the surgeon has a strong sense of directly controlling the tools 26. To this end, position, force, and tactile feedback sensors (not shown) may be employed to transmit position, force, and tactile sensations from the tools 26 back to the surgeon's hands through the input control devices 36.

The Surgeon's Console 16 is usually located in the same room as the patient so that the surgeon may directly monitor the procedure, be physically present if necessary, and speak to an Assistant directly rather than over the telephone or other communication medium. However, the surgeon can be located in a different room, a completely different building, or other remote location from the Patient allowing for remote surgical procedures.

Figure 3:
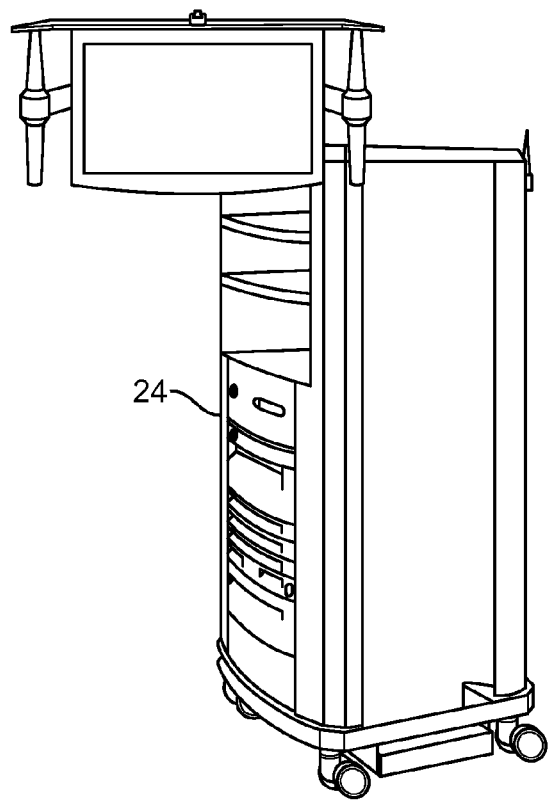
FIG. 3 is a perspective view of the electronics cart of FIG. 1A.

FIG. 3 is a perspective view of the Electronics Cart 24. The Electronics Cart 24 can be coupled with the endoscope 28 and can include a processor to process captured images for subsequent display, such as to a surgeon on the Surgeon's Console, or on another suitable display located locally and/or remotely. For example, where a stereoscopic endoscope is used, the Electronics Cart 24 can process the captured images so as to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations. The surgeon will generally manipulate tissues using the robotic system by moving the controllers within a three dimensional controller work space of controllers of the Surgeon's Console, which in turn, move one or more manipulator arms move through a three dimensional manipulator arm work space. A processor can calculate the position of the manipulator arms in the work space via joint sensors and/or from the movement commands and can affect the desired movement commanded by the surgeon by performing coordinate system transformations to a joint space of the one or more manipulator arms, the joint space being the range of alternative joint configurations available to the processor. The program instructions for effecting these processes may optionally be embodied in a machine readable code stored on a tangible media, which may comprise an optical disk, a magnetic disk, a magnetic tape, a bar code, EEPROM, or the like. Alternatively, programming instructions may be transmitted to and from processor using data communications systems such as an IO cable, an intranet, the internet, or the like. An example control system is described in more detail in U.S. patent application Ser. No. 09/373,678, filed Aug. 13, 1999, the full disclosure of which is incorporated herein by reference.

Figure 4:
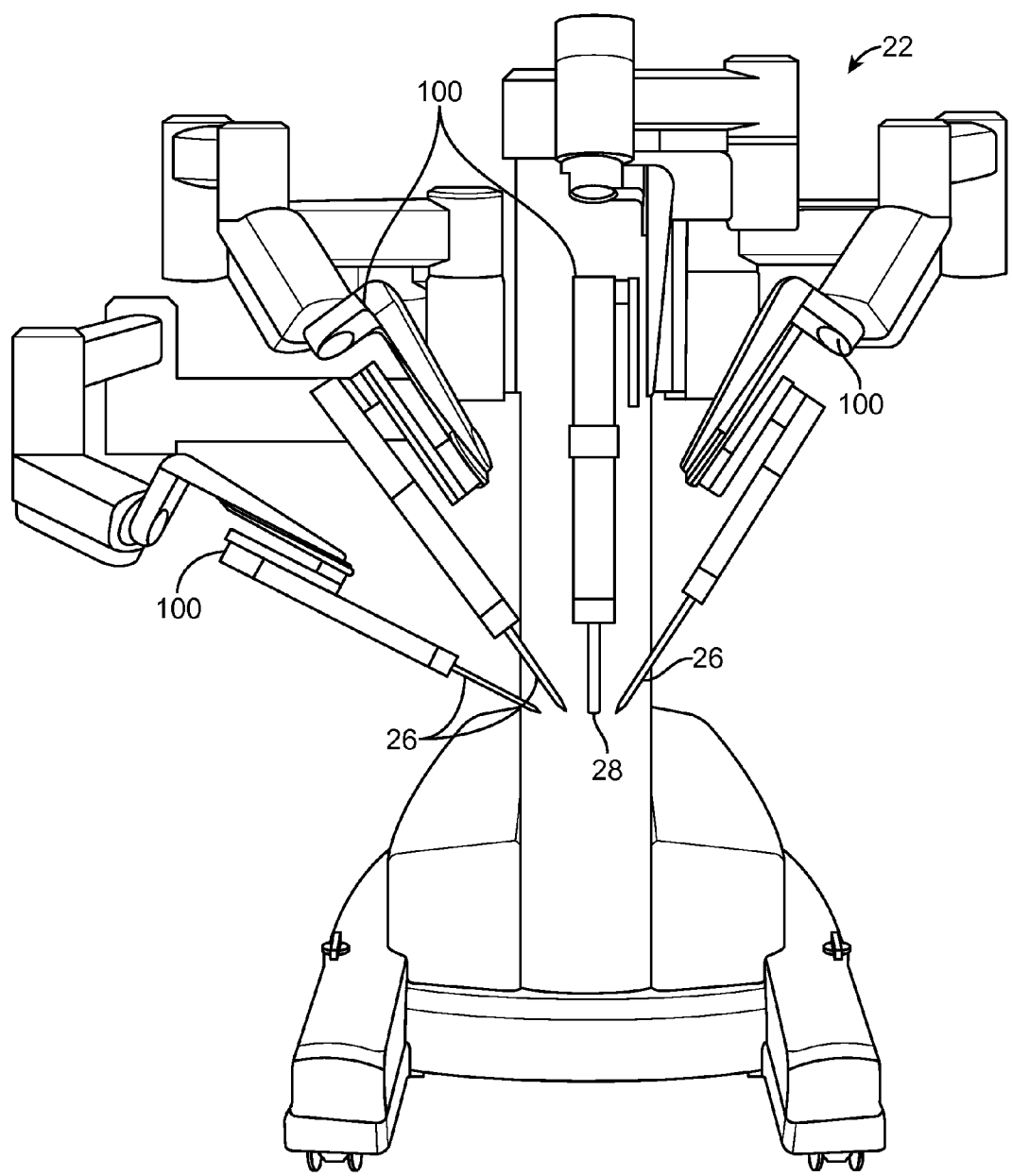
FIG. 4 is a perspective view of a patient side cart having four manipulator arms.

FIG. 4 shows a Patient Side Cart 22 having a plurality of manipulator arms, each supporting a surgical instrument or tool 26 at a distal end of the manipulator arm. The Patient Side Cart 22 shown includes four manipulator arms 100 which can be used to support either a surgical tool 26 or an imaging device 28, such as a stereoscopic endoscope used for the capture of images of the site of the procedure. Manipulation is provided by the robotic manipulator arms 100 having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical instruments or tools 26 when they are positioned within the field-of-view of the imaging device 28.

Regarding surgical tool 26, a variety of alternative robotic surgical tools or instruments of different types and differing end effectors may be used, with the instruments of at least some of the manipulators being removed and replaced during a surgical procedure. Several of these end effectors, including DeBakey Forceps, microforceps, Potts scissors, and clip-applier include first and second end effector elements which pivot relative to each other so as to define a pair of end effector jaws (or blades). For instruments having end effector jaws, the jaws will often be actuated by squeezing the grip members of the handle. Other end effectors, including scalpel and electrocautery probe have a single end effector element (e.g. a single "finger"). Single end effector instruments may also be actuated by gripping of the grip members, for example, so as to trigger the delivery of electrocautery energy to the instrument tip.

At times, the tip of the instrument may be used to capture a tissue image. The elongate shaft of instrument 26 allow the end effectors and the distal end of the shaft to be inserted distally into a surgical worksite through a minimally invasive aperture, often through an abdominal wall or the like. The surgical worksite may be insufflated, and movement of the end effectors within the patient will often be effected, at least in part, by pivoting of the instrument 26 about the location at which the shaft passes through the minimally invasive aperture. In other words, manipulators 100 will move the proximal housing of the instrument outside the patient so that the shaft extends through a minimally invasive aperture location so as to help provide a desired movement of end effector. Hence, manipulators 100 will often undergo significant movement outside patient P during a surgical procedure.

Example manipulator arms in accordance with embodiments of the present invention can be understood with reference to FIGS. 5A-10. As described above, a manipulator arm generally supports a distal instrument or surgical tool and effects movements of the instrument relative to a base. As a number of different instruments having differing end effectors may be sequentially mounted on each manipulator during a surgical procedure (typically with the help of a surgical assistant), a distal instrument holder will preferably allow rapid removal and replacement of the mounted instrument or tool. As can be understood with reference to FIG. 4, manipulators are proximally mounted to a base of the patient side cart. Typically, the manipulator arm includes a plurality of linkages and associated joints extending between the base and the distal instrument holder. In one aspect, an example manipulator includes a plurality of joints having redundant degrees of freedom such that the joints of the manipulator arm can be driven through a range of differing configurations for a given end effector position. This may be the case for any of the embodiments of manipulator arms disclosed herein.

Figure 5A:
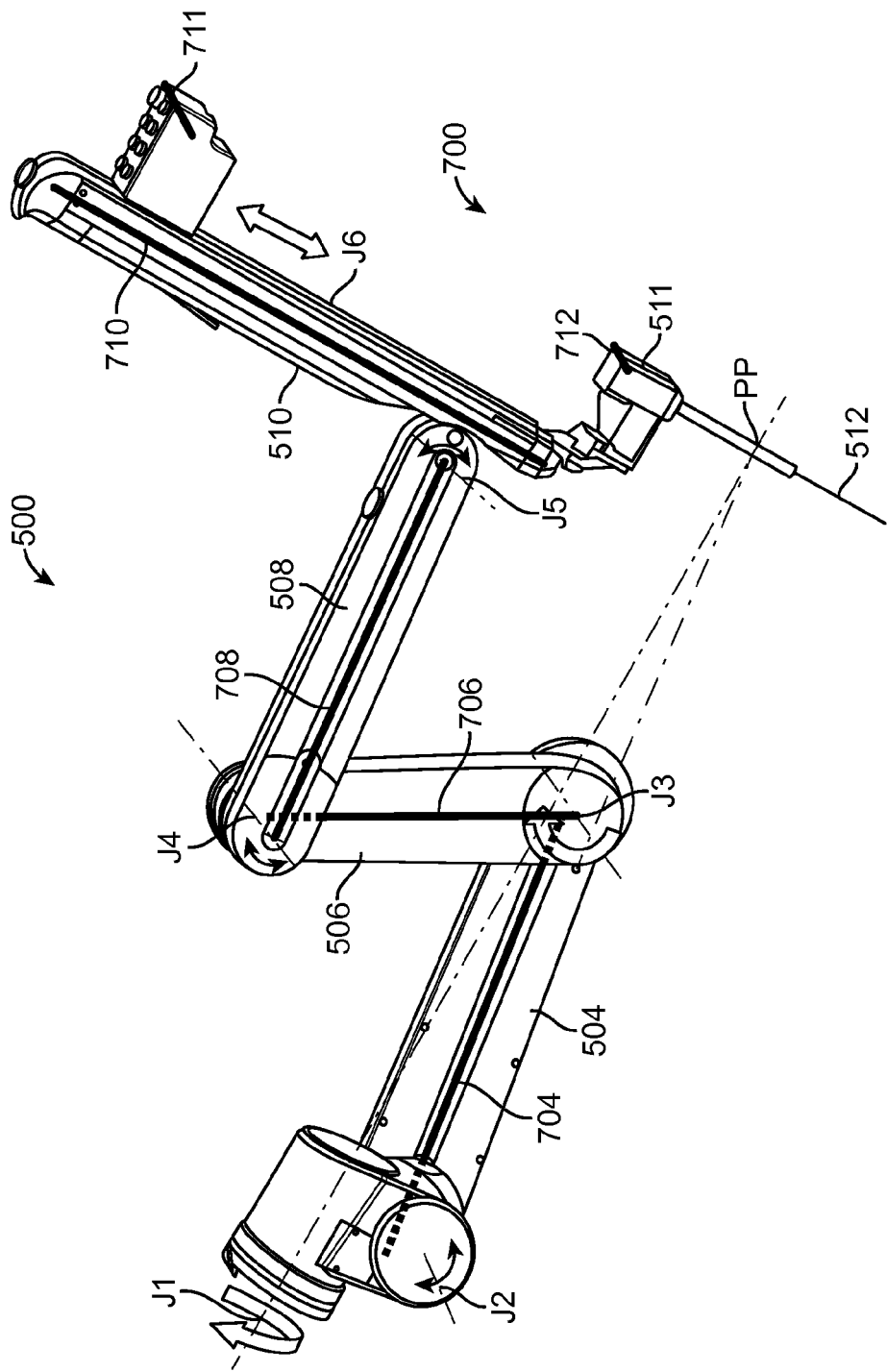
FIGS. 5A-5D show an example manipulator arm.
Figure 5B:
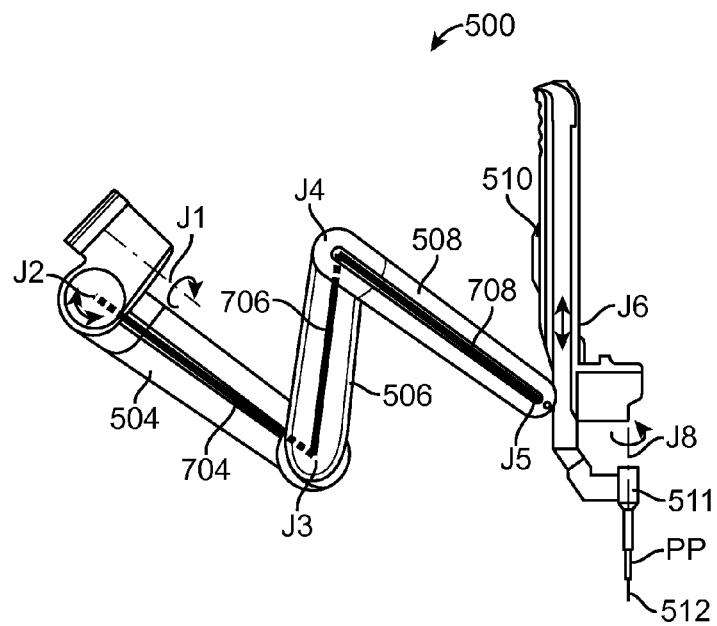

In certain embodiments, such as shown for example in FIG. 5A, an example manipulator arm includes a proximal revolute joint J1 that rotates about a first joint axis so as to revolve the manipulator arm distal of the joint about the joint axis. In some embodiments, revolute joint J1 is mounted directly to the base, while in other embodiments, joint J1 may be mounted to one or more movable linkages or joints. The joints of the manipulator, in combination, have redundant degrees of freedom such that the joints of the manipulator arm can be driven through a range of differing configurations for a given end effector position. For example, the manipulator arm of FIGS. 5A-5D may be maneuvered into differing configurations while the distal member 511 (such as a cannula through which the tool 512 or instrument shaft extends) supported within the instrument holder 510 maintains a particular state and may include a given position or velocity of the end effector. Distal member 511 is typically a cannula through which the tool shaft 512 extends, and the instrument holder 510 is typically a carriage (shown as a brick-like structure that translates on a spar) to which the instrument attaches before extending through the cannula 511 into the body of the patient through the minimally invasive aperture.

Figure 5D:
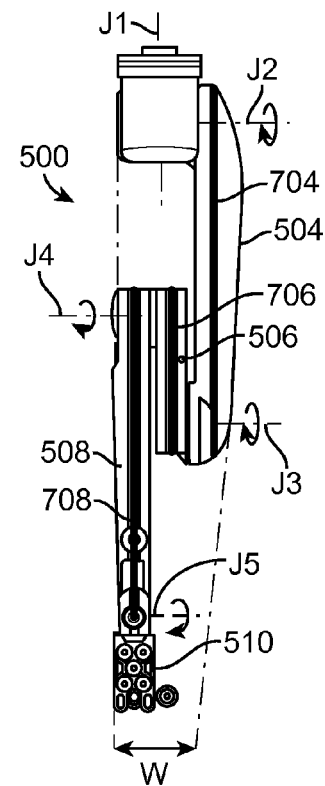
Figure 5C:
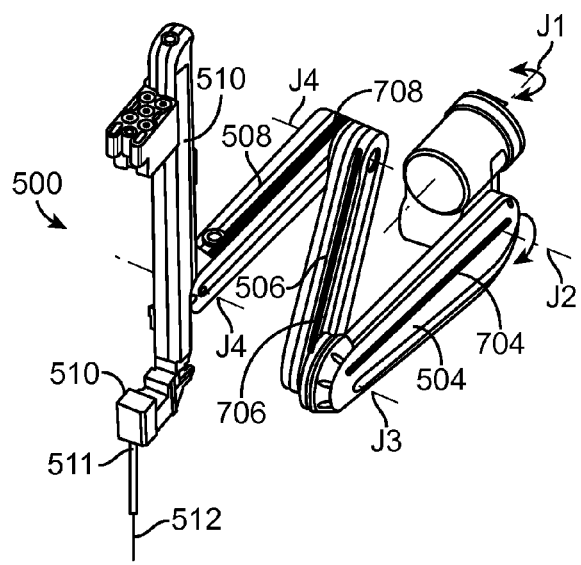

Describing the individual links of manipulator arm 500 of FIGS. 5A-5D along with the axes of rotation of the joints connecting the links as illustrated in FIG. 5A-5D, a first link 504 extends distally from a pivotal joint J2 which pivots about its joint axis and is coupled to revolute joint J1 which rotates about its joint axis. Many of the remainder of the joints can be identified by their associated rotational axes, as shown in FIG. 5A. For example, a distal end of first link 504 is coupled to a proximal end of a second link 506 at a pivotal joint J3 that pivots about its pivotal axis, and a proximal end of a third link 508 is coupled to the distal end of the second link 506 at a pivotal joint J4 that pivots about its axis, as shown. The distal end of the third link 508 is coupled to instrument holder 510 at pivotal joint J5. The pivotal axes of each of joints J2, J3, J4, and J5 may be configured to be substantially parallel such that the linkages appear "stacked" when positioned next to one another, as shown in FIG. 5D, so as to provide a reduced width w of the manipulator arm and improve clearance around a portion of the manipulator during maneuvering of the manipulator assembly. In some embodiments, the instrument holder also includes additional joints, such as a prismatic joint J6, that facilitate axial movement of the instrument through the minimally invasive aperture and facilitate attachment of the instrument holder to a cannula through which the instrument is slidably inserted.

The cannula 511 may include additional degrees of freedom distal of instrument holder 510. Actuation of the degrees of freedom of the instrument may be driven by motors of the manipulator, and alternative embodiments may separate the instrument from the supporting manipulator structure at a quickly detachable instrument holder/instrument interface so that one or more joints shown here as being on the instrument are instead on the interface, or vice versa. In some embodiments, cannula 511 includes a rotational joint J7 (not shown) near or proximal of the insertion point of the tool tip or the remote center RC about which a shaft of the tool pivots adjacent a minimally invasive aperture. A distal wrist of the instrument allows pivotal motion of an end effector through cannula 511 about instrument joints axes of one or more joints at the instrument wrist. An angle between end effector jaw elements may be controlled independently of the end effector location and orientation.

Figure 5E:
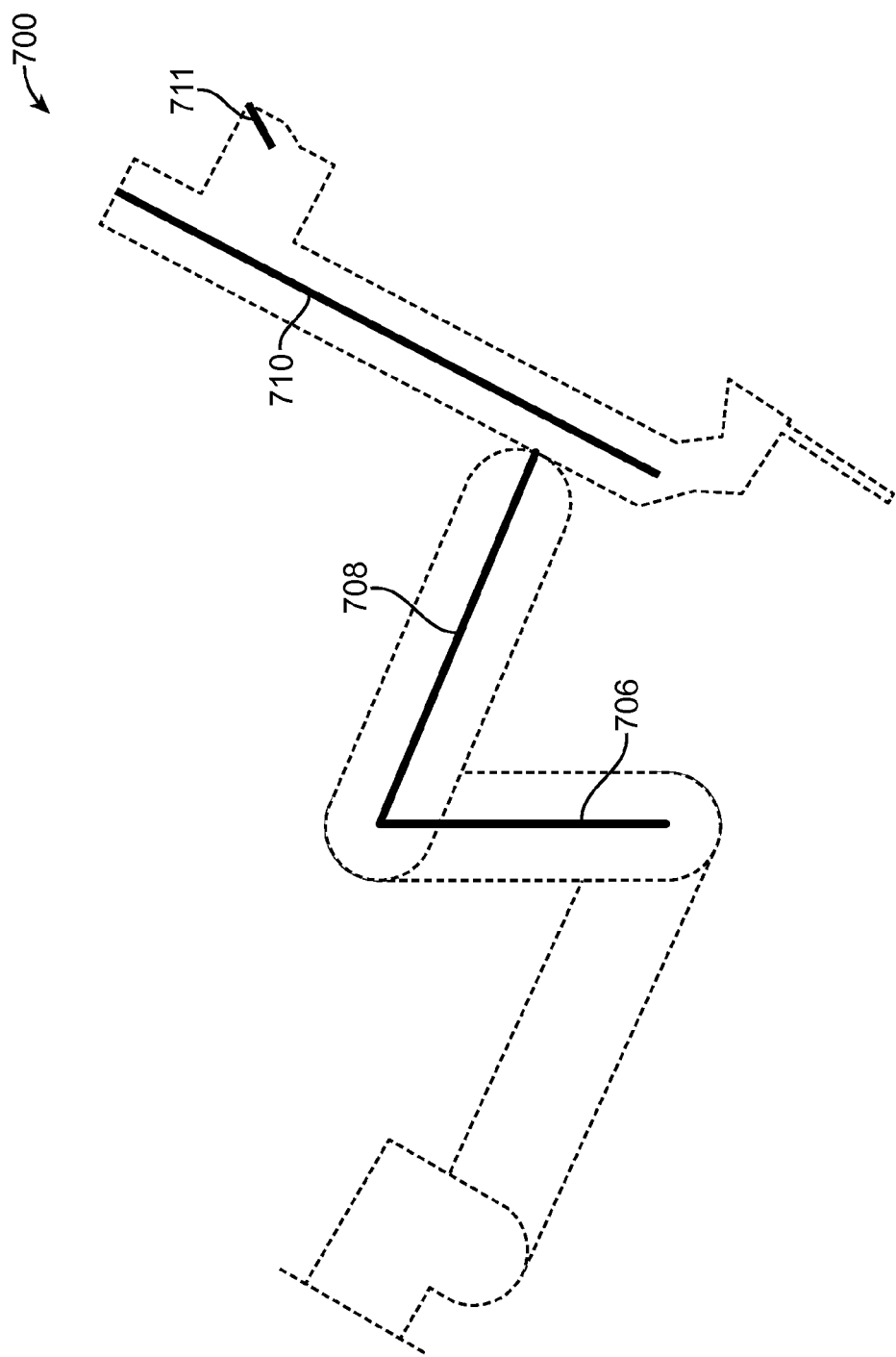
FIG. 5E shows a reference geometry including multiple line segments corresponding to components of the example manipulator arm shown in FIGS. 5A-5D.

In certain embodiments, the system uses a defined reference geometry corresponding to the position or state of each manipulator arm such that a processor of the system can determine when a collision between arms may be imminent by determining a relative state between reference geometries of adjacent manipulator arms. As shown in FIG. 5A, the reference geometry 700, sometimes called an "avoidance reference geometry", can include multiple line segments, 704, 706, 708, 701, 711 each corresponding to a linkage of the physical manipulator arm 500. The "reference geometry" itself is defined by the processor (or previously defined and/or input by a user) and its state is determined and tracked by the processor as the components of the manipulator move throughout a surgical space, typically using joint sensors. The line segments shown in FIG. 5A are for illustrative purposes to indicate how the reference geometry corresponds to the components or feature relating to the manipulator arm and to illustrate variations in how the reference geometry can be defined and utilized by the processor in accordance with the present invention to avoid arm-to-arm collisions. The reference geometry may further include points or line segments that correspond to protrusions or features relating to the manipulator arm, for example, line segment 711 corresponds to a protruding edge of a carriage movably mounted on the spar linkage 710 and line segment 712 corresponds to a protruding edge of the base of the instrument extending through cannula 511. As described herein, the reference geometry line segments defined which correspond to components of a first manipulator are collectively referred to as the "first reference geometry", such as shown in FIG. 5E, which graphically depicts reference geometry 700 as encompassing line segments 706, 708, 710, 711, and 712 that correspond to various components of manipulator arm 500.

Figure 6A:
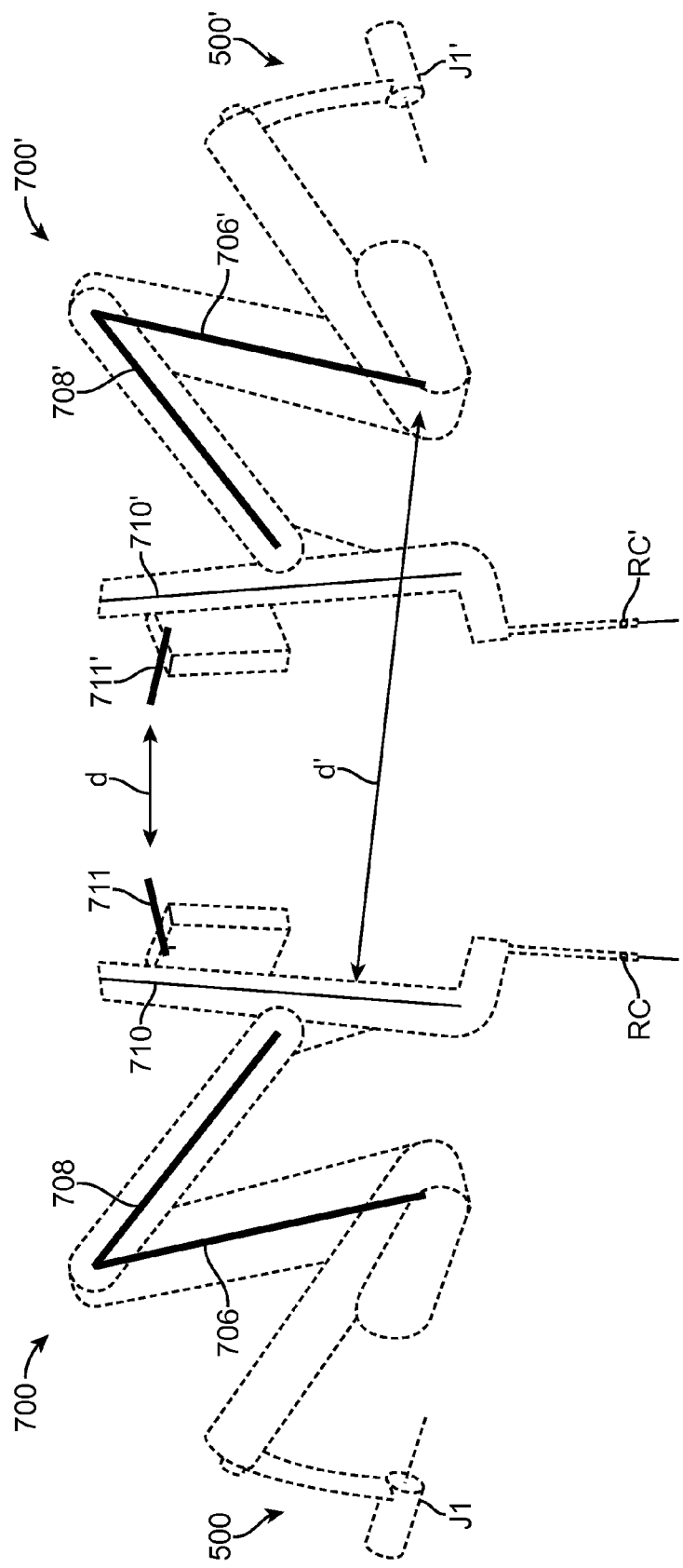
FIGS. 6A-6C show the interaction between a first reference geometry of a first example manipulator arm and a second reference geometry of a second example manipulator arm as used to calculate an avoidance movement for use in driving one or more joints to inhibit collisions between manipulator arms, in accordance with some embodiments.
Figure 6B:
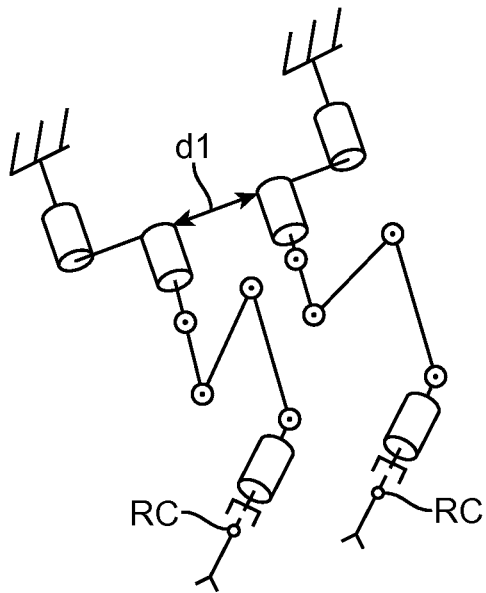
Figure 6C:
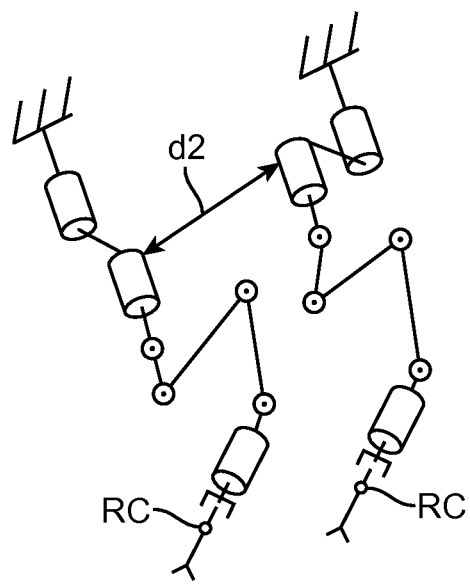

FIGS. 6A-6C illustrate an interaction of a first and second manipulator and an example use of a first and second avoidance reference geometry, as described above, in accordance with the present invention. The system in FIG. 6A includes a first manipulator 500 and a second manipulator 500', each having an identical assembly of kinematically joints linkages having a range of configurations for a given end effector position, although it is appreciated that various other manipulators could be used, as well as combining differing types of manipulators within the same system. In one aspect, the system calculates an avoidance movement of one or both manipulators by applying a virtual force between the line segments of reference geometry 700 and the line segments of reference geometry 700'. The processor uses the virtual force to calculate the joint forces that provide movement needed to move a pair of interacting elements away from one another. In some embodiments, the system may calculate a "repulsion force" between interacting elements of adjacent manipulators using the reference geometries described above along an avoidance vector extending between the interacting elements. The relative state, avoidance vector and repulsion force may be calculated in the three-dimensional workspace of the manipulator arms and then converted into joint space. The movement of the manipulator arm within the joint space is then projected onto a null-space of the Jacobian so as to determine the avoidance movement within the null-space to increase separation between the reference geometries, which correspond to the manipulator structures themselves, while maintaining a desired position of a distal portion of the manipulators. Often, the force may be a function of the relative state or the distance between the reference geometries of each manipulator, a minimum or maximum distance, or a desired distance (e.g., f (d>d_max)=0, f'(d)<0) (note: f' is the derivative of f). Use of a calculated repulsion force between interacting elements of the reference geometries to obtain a null-space coefficients can be used in calculating the avoidance movement within a null-space. The null-space coefficients and calculating of the avoidance movement using the null-space coefficient is described in more detail below.

In an example embodiment, the system determines at least a closest pair of elements from adjacent manipulators that could potentially interact or collide, often called "interacting elements." The pair of interacting elements, one from each manipulator, can include any pair of elements having a range of motion that overlaps. For example, in FIG. 6A, one interacting element pair is 711 and 711', while another interacting element pair is 710 and 706'. In some embodiments, the system only considers interacting element pairs within a specified separation distance. In response to a determination that a distance (d) between interacting element pairs is less than desired, such as the distance (d) between the interacting elements to which reference geometries 711 and 711' correspond, the processor calculates an avoidance movement of one or both manipulators to increase the distance between the interacting elements. In other embodiments, the calculation of avoidance movement may also include forces obtained using distances between other pairs of interacting elements, such as distance d' between 710 and 706' so as to provide more efficient movement or maintain a suitable distance between other interacting element pairs during movement. In certain embodiments, the avoidance movement is calculated by determining a repulsion force along a vector extending between the identified interaction elements or applying a virtual force in the work space of the manipulators and using this form to calculate the avoidance movement within the joint space.

In some embodiments, the avoidance movement is calculated so as to drive the joints of one manipulator of a pair used in the above calculations according to the calculated avoidance movement. In other embodiments, the avoidance movement may be calculated so as to drive one more particular joints of a manipulator, regardless of whether those joints are driven to effect other calculated movements. Additionally, avoidance movement may also be calculated to drive one or more particular joints of the manipulator arm, such as a joint that is not driven when effecting a displacing movement of the manipulator arm commanded by a user.

In the embodiment of FIG. 6A, in response to a determination that the distance (d) is less than desired, the processor determines the calculated avoidance movement of the second manipulator 500' to increase the distance (d) between reference geometries 711 and 711'. As shown in FIG. 6A, the manipulator arms are each supported by a proximal revolute joint J1 that pivots the respective arm about an axis of the joint. As shown in FIGS. 6B-6C, movement of one or both manipulator arms using a combination of joints in one or both arms, respectively, can move an upper portion of the arm without changing the state of the end effector and its remote center RC. In FIG. 6B, the nearest points are determined by the system to be a distance (d1) apart. In response to this determination (or according to any of the methods described herein), the system drives one or more joints of one or both arms to increase the distance between nearest points (shown as d2 in FIG. 6C) without changing the state of the end effector at the end of each arm; thus, the system avoids a collision by driving at least a first joint of one of a pair of manipulators according to a calculated movement within a null-space of the Jacobian. In some embodiments, driving at least a first proximal joint may provide the avoidance movement while minimizing reconfiguration of a distal portion (e.g. end effector) of the manipulator, although a similar avoidance movement could be calculated to drive one or more joints of a more distal portion of the manipulator arm. In another aspect, the system may be configured to calculate the avoidance movement to move any of the joints described herein, whether or not such joints are driven when effecting displacing movement, or to include driving of joints according to hierarchy based on a particular configuration or state of the manipulator.

In accordance with certain embodiments, avoidance movement may be calculated according to a number of differing methods, which often include determining "nearest points" between manipulator arms. The nearest points can be determined either using calculations based on known manipulator positions or states via joint sensors or can be approximated using other suitable means, such as an external sensor, video, sonar, capacitive, or touch sensors, and the like. Embodiments may also use proximity sensors mounted on the driven linkages or slaves that can sense local arm-to-arm proximity and/or collisions.

In certain embodiment, the processor determines the nearest points on the line segments of each reference geometry. After applying the virtual repulsion force, the processor then calculates the repulsion force between the first and second manipulator. In one aspect, the reference geometry of each manipulator arm may be defined as "local line segments" such that interacting line segments on adjacent manipulator arms repel one another. In another aspect, the reference geometry of one manipulator may be defined as "local line segments" and the other as "obstacle line segments," such that only the local line segments are repelled by the virtual force. This aspect allows the system to avoid collisions by calculating an avoidance movement for only one or only some of the manipulator arms, thereby preventing unnecessary movement or overly complex avoidance movements. For example, although the virtual force may be applied between line segments of each reference geometry, only the movement of the "local line segments" is calculated. In some embodiments, the processor converts the calculated forces obtained from applying the virtual force to joint velocities of the manipulator arms to be moved to according to the avoidance movement, which is then projected onto the null-space. This allows an avoidance movement to be calculated using the virtual force that extends the joints and/or links of the manipulator within a null-space of the Jacobian so as to maintain the desired end effector while simultaneously avoiding arm-to-arm collisions.

In an example embodiment, the processor determines a distance between at least one pair of reference geometry line segments from each manipulator arm, typically the nearest pair of line segments, often using a calculation within the work space of the manipulator arms. For line segment pairs that are closer than a certain maximum exclusion distance, the closest points are identified. The processor then applies a virtual repulsion vector, the strength of which is inversely proportional to the distance, which is then converted into the joint space and projected onto the null-space so as to calculate the movement within the null-space to maintain sufficient clearance between the line segment of the pair. The processor may perform the above process to more than one line segment pair. In such embodiments, the combined result of the repulsion vectors from all line segment pairs can be consolidated into a final set of null-space coefficients ($\alpha$), which may then be used by the joint controller to effect the calculated avoidance movement. Use of the null-space coefficients to effect movement within a null-space is described in further detail below.

In another example embodiment, for each pair of manipulator arms, the processor first determines a pair of elements or components which could potentially contact or collide with one another using reference geometries corresponding to each elements, as described above. Using the corresponding reference geometries, the system then determines the closest elements of each pair, multiple interaction pairs, or a weighted sum of the effects of all element pairs, typically within a maximum exclusion distance. To calculate the avoidance movement, the processor generally first determines the nearest points on each pair of interaction elements and calculates an avoidance vector that may be used to "push" the elements away from each other. The avoidance vector may be calculated by generating a virtual force as described above and commanded a velocity in a direction to repel the elements from each other, or by various other methods. The processor then maps the forces needed to repel the elements away from each other at the nearest points of the reference geometries into null-space vectors to obtain null-space coefficients, which are then used to calculate the avoidance movement within the null-space of the manipulator.

In one approach, the processor calculates an avoidance vector in a work space of the manipulator arms; transforms the avoidance vectors into the joint velocity space; and then projects the vectors onto the null-space using the result to obtain the avoidance movement. The processor may be configured to calculate a repulsion or avoidance vector between nearest points; map the avoidance vector into the motion of the "nearest" point of the manipulator arms, in the work space, and then determine the null-space coefficients ($\alpha$) that provide the desired direction and magnitude to move the nearest points away from one another. If multiple interacting points are used between various points or features on adjacent manipulator arms, the resulting null-space coefficients associated with the avoidance vectors from each interacting feature can be combined through summation.

In another approach, the processor may use null-space basis vectors; transform the vectors into the motion of the avoidance geometry of the manipulator in the physical space; and then combine these and the avoidance vectors in the physical space into coefficients for the original null-space basis vectors. The processor may be configured to calculate a repulsion or avoidance vector between nearest points of the manipulator arms (e.g. avoidance geometries), and combine these with the avoidance vectors, as was just described. If multiple features on the manipulator arms are used, the resulting joint velocity vector or null-space coefficients can be combined using least-squares or other methodology.

In a first approach, the avoidance movement is determined by generating an potential field in joint-space, such that high potentials represent shorter distances between the manipulator arms and lower potentials represent larger distances. The null-space coefficients ($\alpha$) are then chosen to descend down the negative gradient of the potential field, preferably to the greatest extent possible. In a second approach, the system determines the null-space basis vectors and maps the null-space basis vectors into the resulting motion of the avoidance geometry in the work space, and then selecting the null-space coefficients for each basis vector increase the distance between the avoidance geometries of the manipulator arms, thereby increasing the distance between the nearest points on the manipulator arms.

As described above, the avoidance movement may be calculated so as to include driving of any number of joints of differing types, or alternatively, to avoid driving particular joints of the manipulator arm. Additional joints which may be used in varying degrees in accordance with the present invention are shown in FIGS. 7-10 and described further below.

Figure 7:
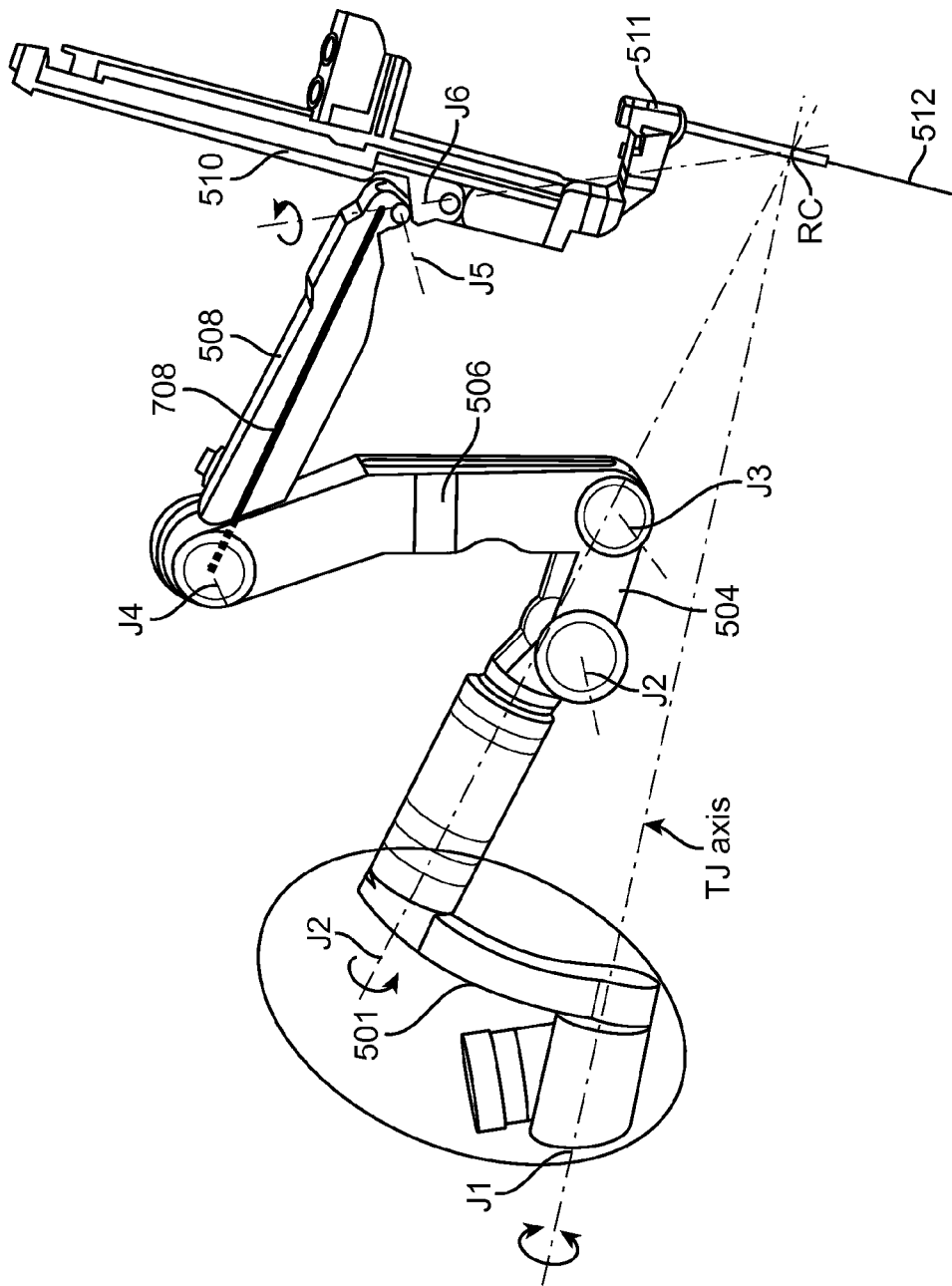
FIG. 7 shows an example manipulator arm having a proximal revolute joint that revolves the manipulator arm about an axis of the joint.
Figure 8:
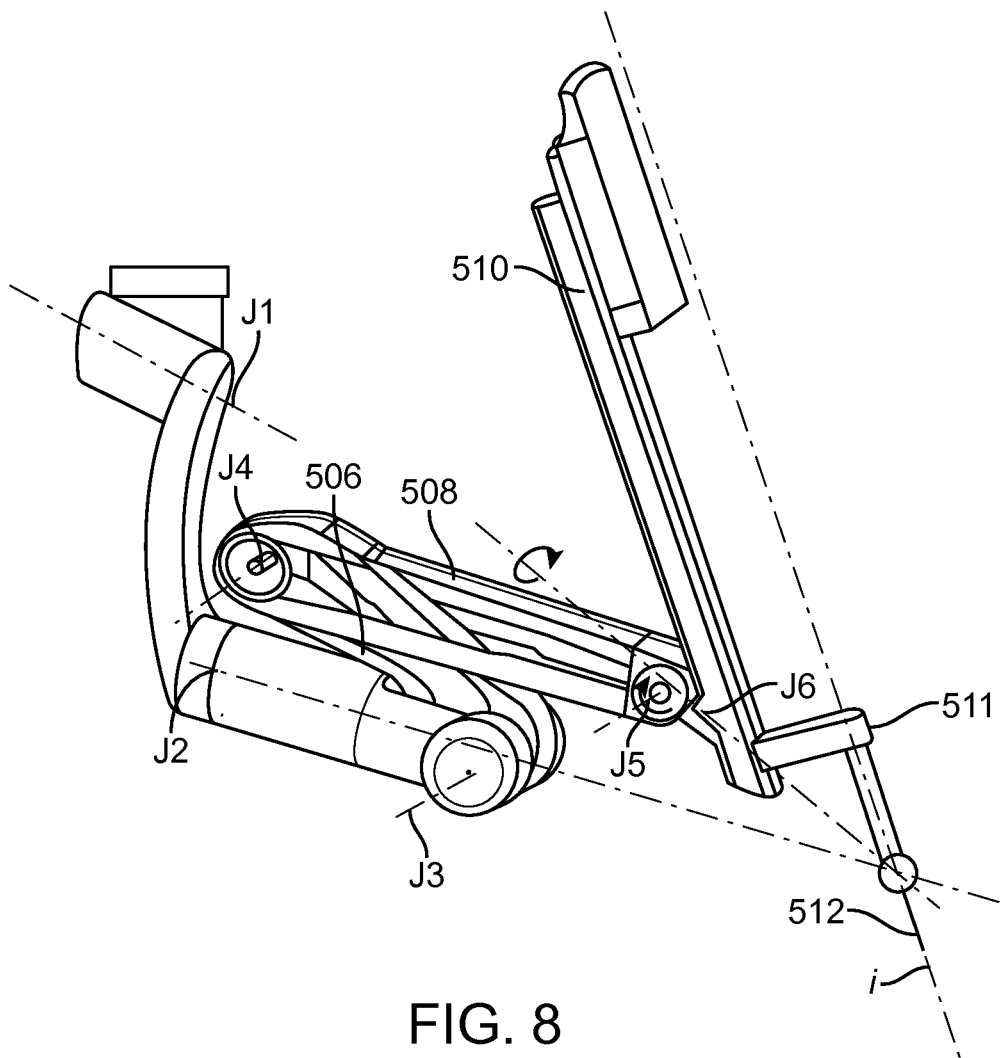
FIG. 8 shows an example manipulator arm having a twisting joint near the distal instrument holder that revolves or twists the instrument holder about the joint axis.

In the manipulator arm shown in FIG. 7, the avoidance movement could be calculated to include driving various combinations of joints J1, J2, J3, J4 and J5 (in the depicted embodiment joints J3, J4 and J5 are configured in a parallelogram arrangement, and therefore move together and have a single state between them), or alternatively could be calculated to drive joint J6, as well as any other joints that provide the needed manipulator arm within the null-space. Joint J6 of the manipulator arm illustrated in FIG. 7 may optionally be used as the joint coupling the instrument holder 510 to a distal link of the manipulator arm 508. Joint J6 allows the instrument holder 510 to twist or rotate about the axis of joint J6, the axis typically passing through the remote center or insertion point. Ideally, the joint axis is located distally on the arm and is therefore particularly well suited to moving the orientation of the insertion axis. The addition of this redundant axis allows the manipulator to assume multiple positions for any single instrument tip position, thereby allowing the instrument tip to follow the surgeon's commands while simultaneously avoiding collisions with adjacent manipulator arms or other obstacles. The manipulator arm may be configured to articulate an end effector of the mounted surgical instrument around a first axis (e.g., the pitch axis) and to articulate the end effector around a second axis (e.g., the yaw axis) that is perpendicular to the first axis. The relationship between the joint axis of joint J6, the yaw axis of J1 and the insertion axis of cannula 511 is shown in FIG. 8.

FIG. 7 also illustrates a manipulator having a proximal revolute joint J1 that revolves the manipulator arm about a joint axis of the revolute joint. Joint J1 includes a link 501 that offsets the next successive joint by a pre-determined distance or angle. Typically, the joint axis of joint J1 is aligned with the remote center RC or insertion point of the tool tip, as shown in each of FIG. 7. In an example embodiment, the joint axis of joint J1 passes through the remote center, as does each other revolute joint axis in the manipulator arm, to prevent motion at the body wall and can therefore be moved during surgery. The joint axis is coupled to a proximal portion of the arm so it can be used to change the position and orientation of the back of the arm. In general, redundant axes, such as this, allow the instrument tip to follow the surgeon's commands while simultaneously avoiding collisions with other arms or patient anatomy.

Figure 9:
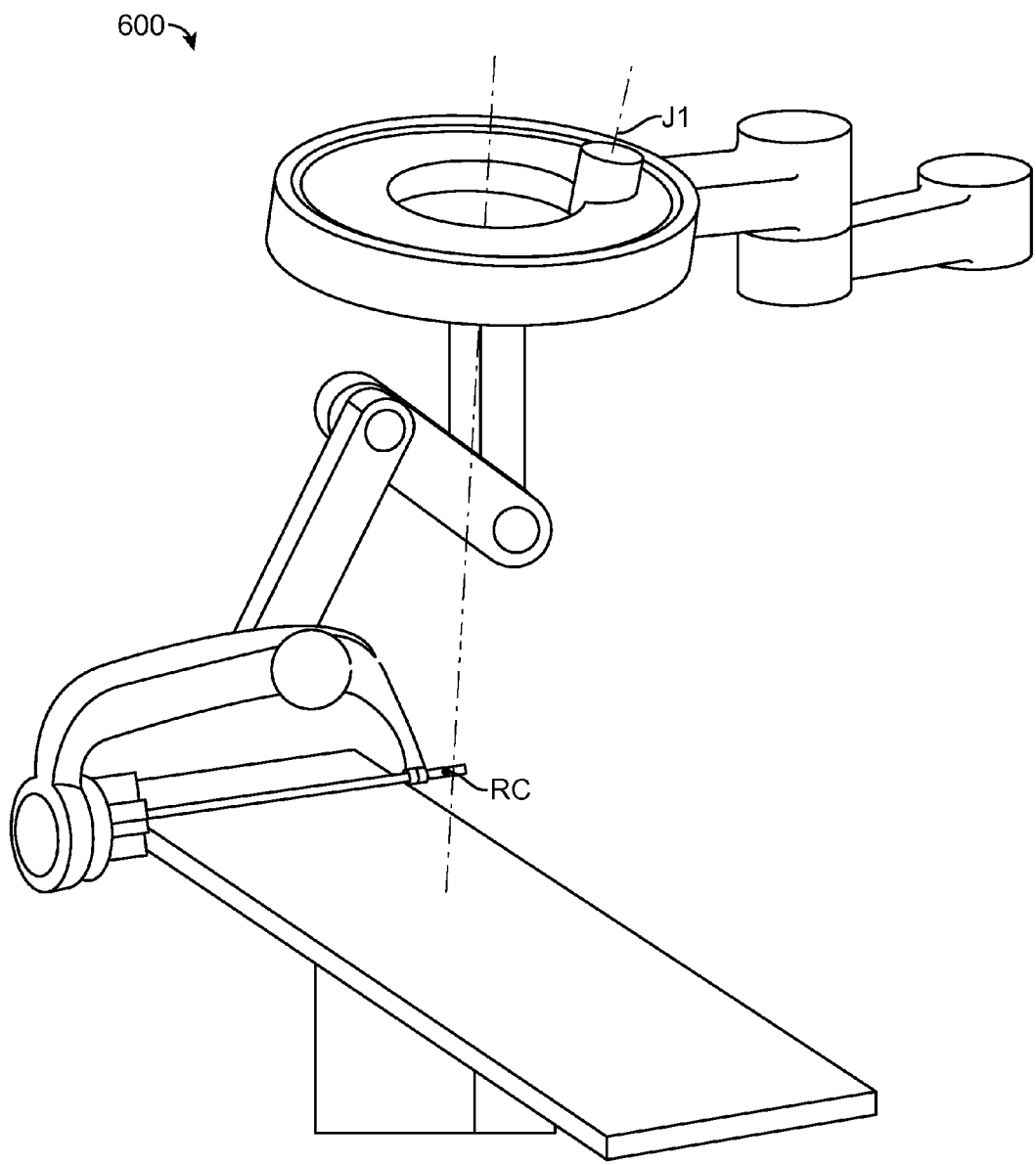
FIGS. 9-10 show example manipulator arms having a proximal revolute joint supporting the manipulator arm that translates about a curved path.
Figure 10:
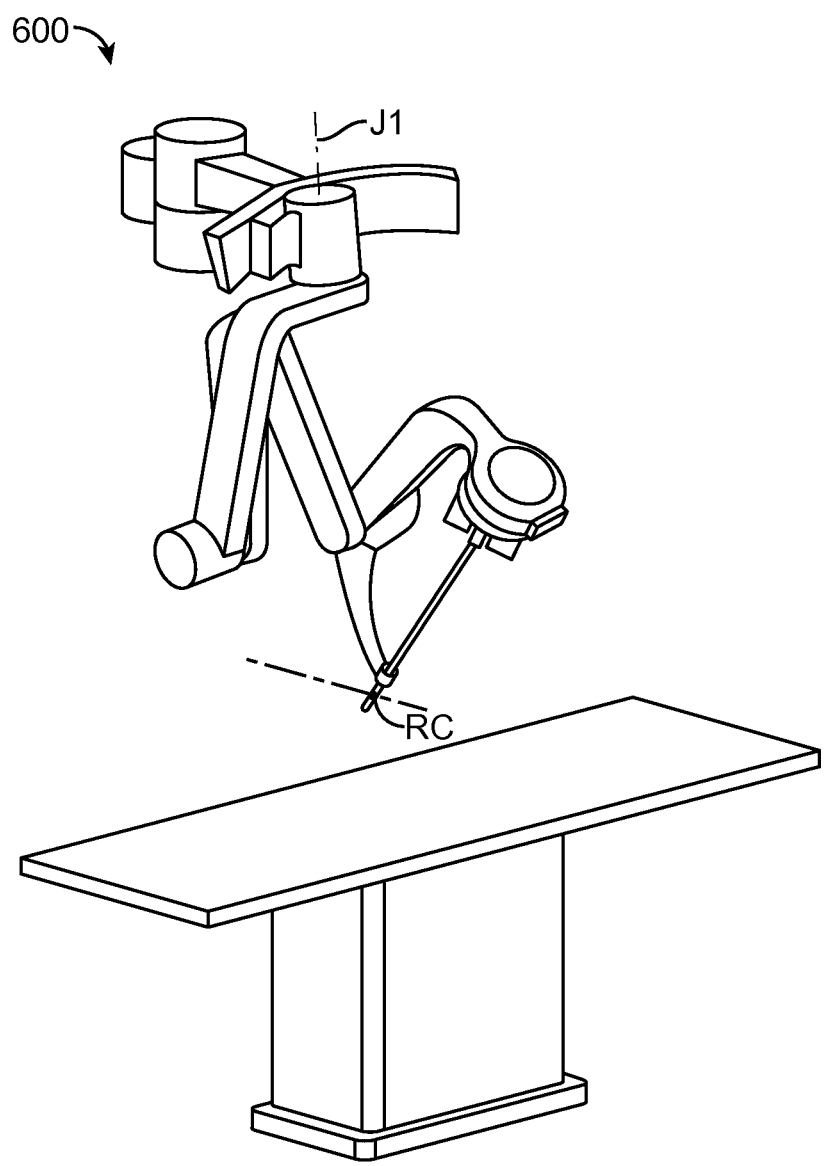

FIGS. 9-10 illustrate another type of redundant joint for use with example manipulator arms, a proximal joint that translates or revolves the manipulator arm about an axis. In some embodiments, the first joint J1, which supports the manipulator arm, translates along a curved path so as to increase the range of motion of the manipulator arm and away from areas in which the manipulator arm may have decreased maneuverability. This joint may include a circular path, such as shown in FIG. 9, or may a semi-circular or arcuate path, such as shown in FIG. 10. Generally, in such embodiments, the joint axis intersects with the remote center RC about which the shaft of the tool tip pivots. In the embodiment shown in FIG. 9, the joint axis is a vertical axis, whereas in the embodiment shown in FIG. 10 the joint axis is horizontal.

In an example embodiment, the joint movements of the manipulator are controlled by driving one or more joints by a controller using motors of the system, the joints being driven according to coordinated and joint movements calculated by a processor of the controller. Mathematically, the controller may perform at least some of the calculations of the joint commands using vectors and/or matrices, some of which may have elements corresponding to configurations or velocities of the joints. The range of alternative joint configurations available to the processor may be conceptualized as a joint space. The joint space may, for example, have as many dimensions as the manipulator has degrees of freedom, and a particular configuration of the manipulator may represent a particular point in the joint space with each coordinate corresponding to a joint state of an associated joint of the manipulator.

In certain embodiments, the system includes a controller in which a commanded position and velocity within the Cartesian-coordinate-space (referred to herein as Cartesian-space) are inputs. Although generally, there is no closed form relationship which maps a desired Cartesian-space position to an equivalent joint-space position, there is generally a closed form relationship between the Cartesian-space and joint-space velocities, such that a kinematic Jacobian can be used to map joint-space velocities to Cartesian-space velocities. Thus, even when there is no closed-form mapping between input and output positions, mappings of the velocities of the joint can iteratively be used, such as in a Jacobian-based controller to implement a movement of the manipulator from a commanded user input, however, a variety of implementations can be used.

In an example embodiment, the system includes a controller in which a commanded position and velocity of a feature in the work-space, denoted here as its Cartesian space, are inputs. The feature may be any feature on the manipulator or off the manipulator which can be used as a control frame to be articulated using control inputs. An example of a feature on the manipulator, used in some embodiments described herein, would be the tool-tip. Another example of a feature on the manipulator would be a physical feature which is not on the tool-tip, but is a part of the manipulator, such as a pin or a painted pattern. An example of a feature off the manipulator would be a reference point in empty space which is exactly a certain distance and angle away from the tool-tip. Another example of a feature off the manipulator would be a target tissue whose position relative to the manipulator can be established. In all these cases, the end effector is associated with an imaginary control frame which is to be articulated using control inputs. However, in the following, the "end effector" and the "tool tip" are used synonymously. Although generally, there is no closed form relationship which maps a desired Cartesian space end effector position to an equivalent joint-space position, there is generally a closed form relationship between the Cartesian space end effector and joint-space velocities. The kinematic Jacobian is the matrix of partial derivatives of Cartesian space position elements of the end effector with respect to joint space position elements. In this way, the kinematic Jacobian captures the kinematic relationship between the end effector and the joints. In other words, the kinematic Jacobian captures the effect of joint motion on the end effector. The kinematic Jacobian (J) can be used to map joint-space velocities (dq/dt) to Cartesian space end effector velocities (dx/dt) using the relationship below:

$$dx/dt = J\,dq/dt$$

Thus, even when there is no closed-form mapping between input and output positions, mappings of the velocities can iteratively be used, such as in a Jacobian-based controller to implement a movement of the manipulator from a commanded user input, however a variety of implementations can be used. Although some embodiments include a Jacobian-based controller, some implementations may use a variety of controllers that may be configured to access the Jacobian to provide any of the features described herein.

One such implementation is described in simplified terms below. The commanded joint position is used to calculate the Jacobian (J). During each time step ($\Delta t$) a Cartesian space velocity (dx/dt) is calculated to perform the desired move ($dx_{des}/dt$) and to correct for built up deviation ($\Delta x$) from the desired Cartesian space position. This Cartesian space velocity is then converted into a joint-space velocity (dq/dt) using the pseudo-inverse of the Jacobian ($J^\#$). The resulting joint-space commanded velocity is then integrated to produce joint-space commanded position (q). These relationships are listed below:

$$dx/dt = dx_{des}/dt + k\Delta x \qquad (1)$$

$$dq/dt = J^\# dx/dt \qquad (2)$$

$$q_i = q_{i-1} + dq/dt\,\Delta t \qquad (3)$$

The pseudo-inverse of the Jacobian (J) directly maps the desired tool tip motion (and, in some cases, a remote center of pivotal tool motion) into the joint velocity space. If the manipulator being used has more useful joint axes than tool tip degrees of freedom (up to six), (and when a remote center of tool motion is in use, the manipulator should have an additional 3 joint axes for the 3 degrees of freedom associated with location of the remote center), then the manipulator is said to be redundant. A redundant manipulator's Jacobian includes a "null-space" having a dimension of at least one. In this context, the "null-space" of the Jacobian (N(J)) is the space of joint velocities which instantaneously achieves no tool tip motion (and when a remote center is used, no movement of the pivotal point location); and "null-motion" is the combination, trajectory or path of joint positions which also produces no instantaneous movement of the tool tip and/or location of the remote center. Incorporating or injecting the calculated null-space velocities into the control system of the manipulator to achieve the desired reconfiguration of the manipulator (including any reconfigurations described herein) changes above equation (2) to the following:

$$dq/dt = dq_{perp}/dt + dq_{null}/dt \qquad (4)$$

$$dq_{perp}/dt = J^\# dx/dt \qquad (5)$$

$$dq_{null}/dt = (1 - J^\# J)z = V_n V_n^T z = V_n \alpha \qquad (6)$$

The joint velocity according to Equation (4) has two components: the first being the null-perpendicular-space component, the "purest" joint velocity (shortest vector length) which produces the desired tool tip motion (and when the remote center is used, the desired remote center motion); and the second being the null-space component. Equations (2) and (5) show that without a null-space component, the same equation is achieved. Equation (6) starts with a traditional form for the null-space component on the left, and on the far right side, shows the form used in an example system, wherein ($V_n$) is the set of orthonormal basis vectors for the null-space, and ($\alpha$) are the coefficients for blending those basis vectors. In some embodiments, $\alpha$ is determined by control parameters, variables or setting, such as by use of knobs or other control means, to shape or control the motion within the null-space as desired.

Figure 11A:
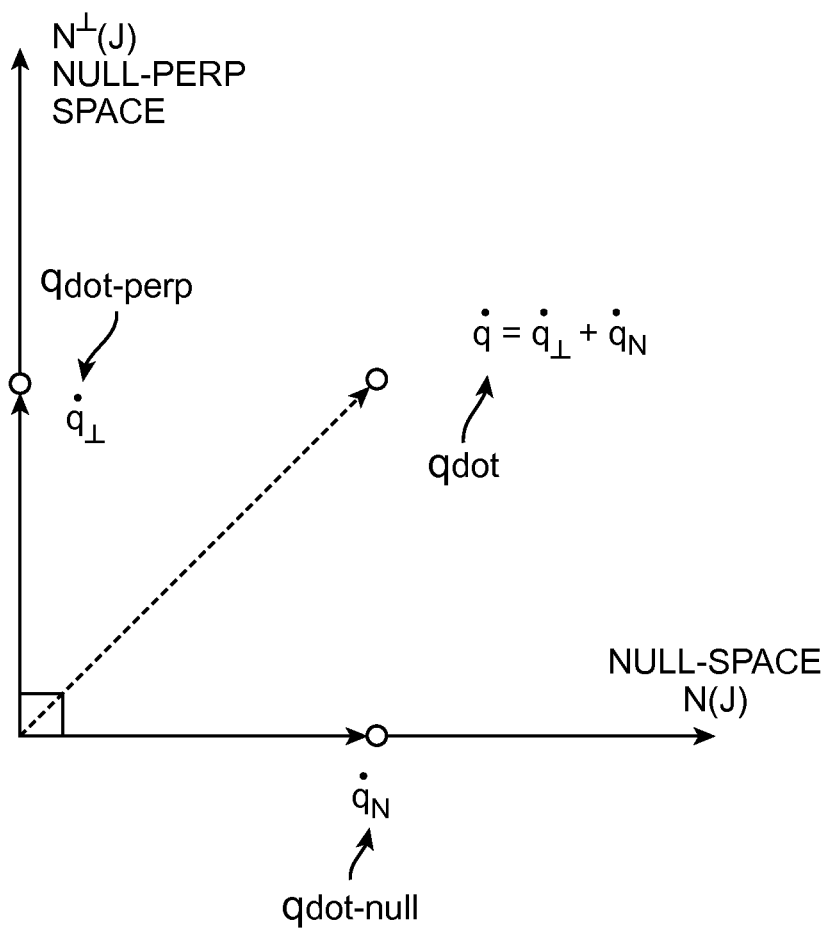
FIG. 11A graphically represent the relationship between the null-space and the null-perpendicular space of the Jacobian in an example manipulator assembly, and FIG. 11B graphically represents the relationship between the null-space and the null-motion manifold.

FIG. 11A graphically illustrates the relationship between the null-space of the Jacobian and the null-perpendicular-space of the Jacobian in an example manipulator arm. FIG. 11A shows a two-dimensional schematic showing the null-space along the horizontal axis, and the null-perpendicular space along the vertical axis, the two axes being orthogonal to one another. The diagonal vector represents the sum of a velocity vector in the null-space and a velocity vector in the null-perpendicular space, which is representative of Equation (4) above.

Figure 11B:
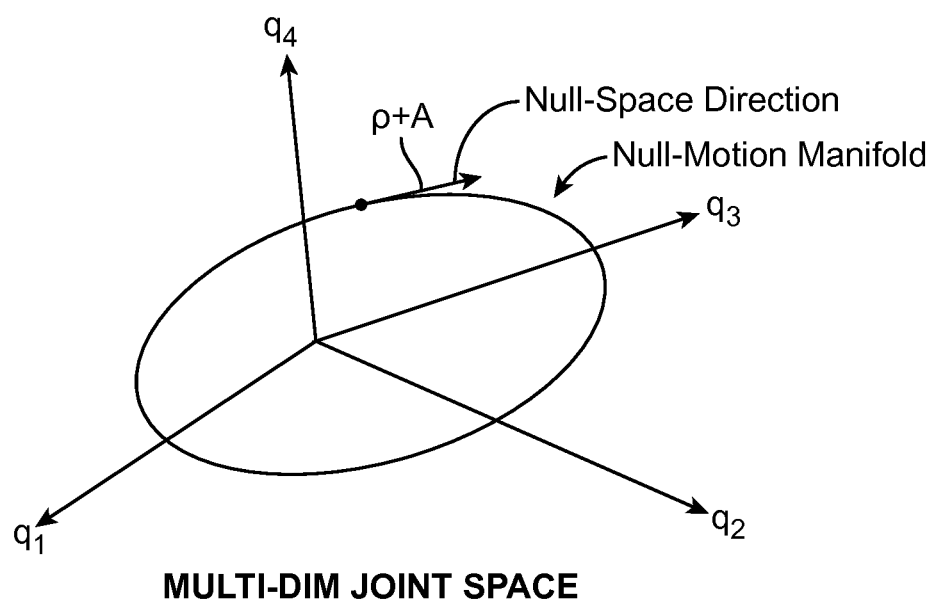

FIG. 11B graphically illustrates the relationship between the null-space and the null-motion manifold within a four-dimensional joint space, shown as the "null-motion manifold." Each arrow (q1, q2, q3, and q4) representing a principal joint axis. The closed curve represents a null-motion manifold which is a set of joint-space positions which instantaneously achieves the same end effector state (e.g. position). For a given point A on the curve, since the null-space is a space of joint velocities which instantaneously produce no movement of the end effector, the null-space is parallel to the tangent of the null-motion manifold at point A. In an example embodiment, calculating the avoidance movement includes generating null-space coefficients ($\alpha$) which increase the distance between the interaction element pairs as determined using the first and second reference geometries, thereby increasing the distance between manipulator arms.

Figure 12:
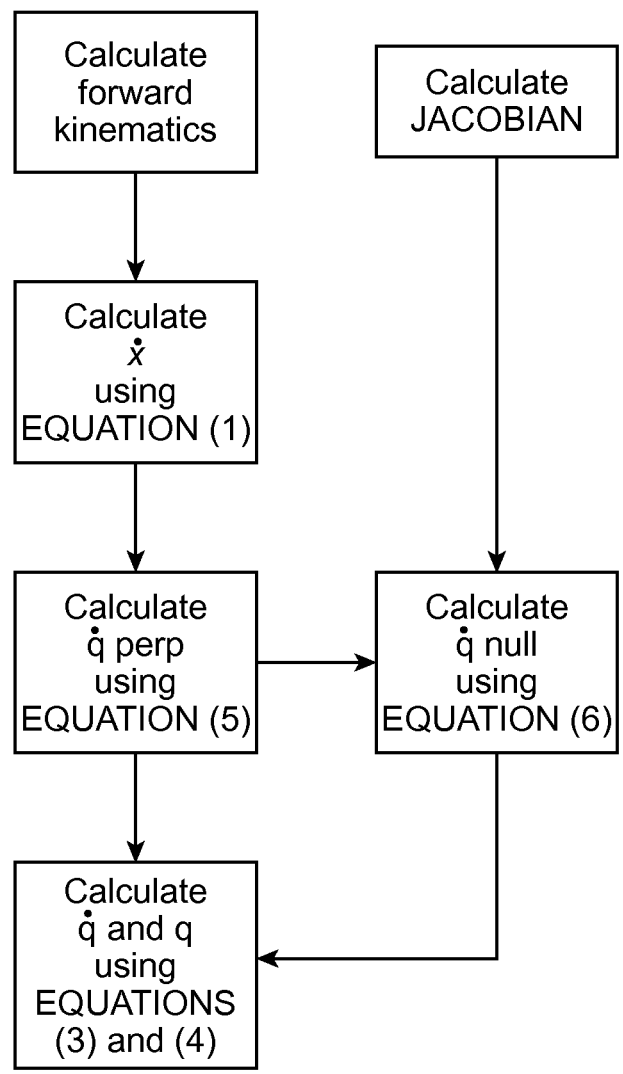
FIGS. 12-13 are simplified block diagrams representing methods in accordance with some embodiments.
Figure 13:
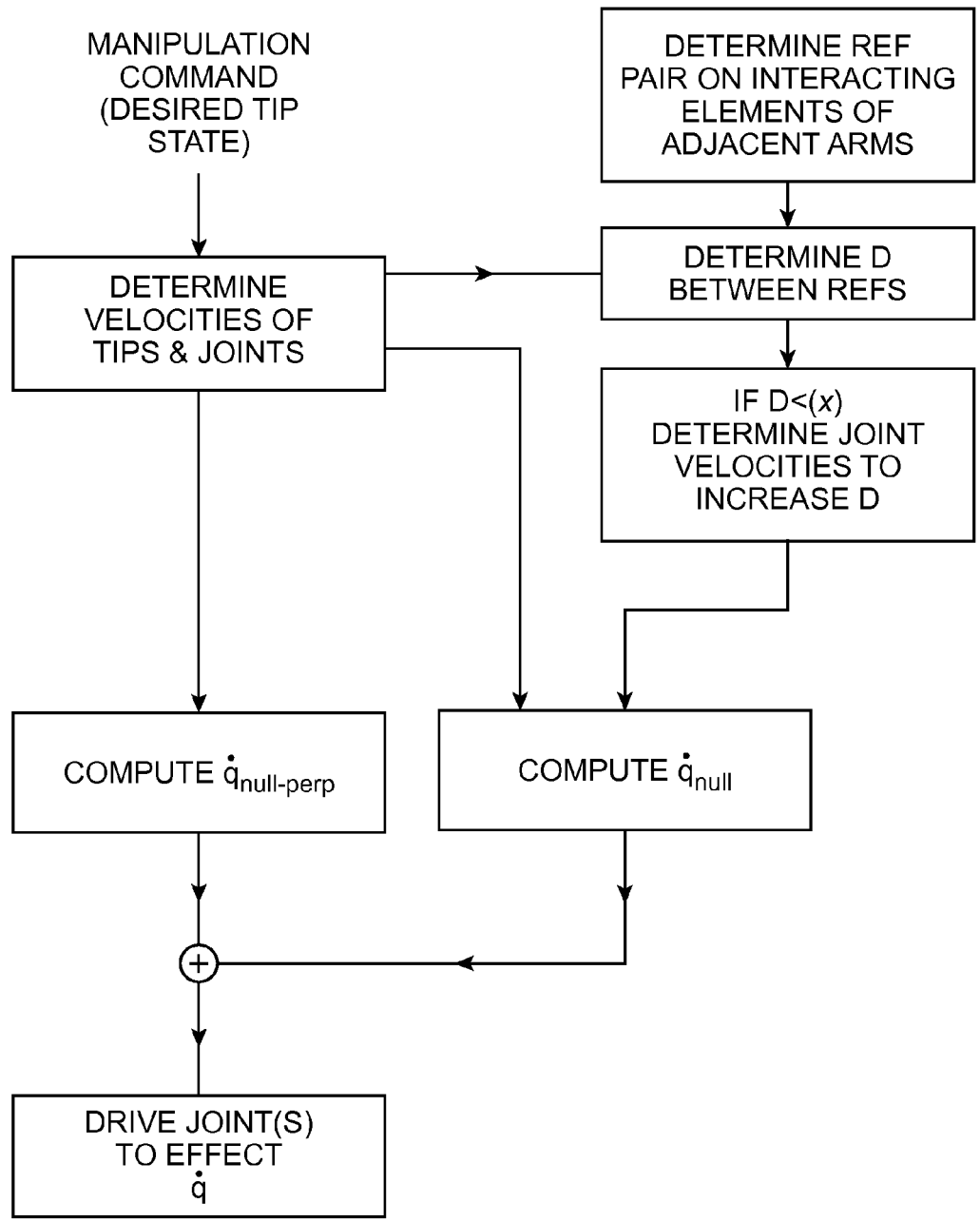

FIGS. 12-13 illustrate methods of reconfiguring a manipulator assembly of a robotic surgical system to avoid arm-to-arm collisions in accordance with embodiments of the present invention. FIG. 12 shows a simplified schematic of the required blocks need to implement the general algorithms to control the patient side cart joint states, in relation to the equations discussed above. According to the method of FIG. 12, the system: calculates the forward kinematics of the manipulator arm; then calculates dx/dt using Equation (1), calculates $dq_{perp}/dt$ using Equation (5), then calculates $dq_{null}/dt$ using Equation (6). From the calculated $dq_{perp}/dt$ and $dq_{null}/dt$ the system then calculates dq/dt and q using Equations (4) and (3), respectively, thereby providing the movement by which the controller effects the avoidance movement of the manipulator while maintaining the desired commanded state of the end effector (and/or location of the remote center).

Figure 14:
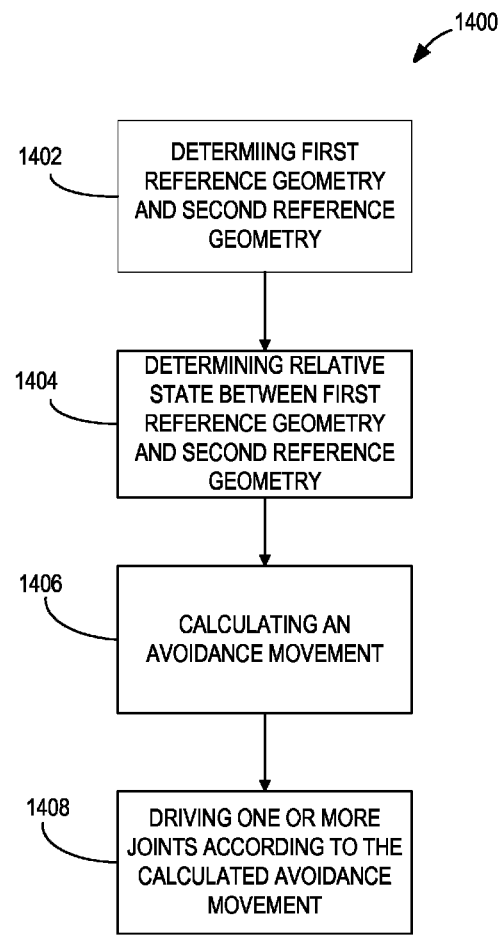
FIG. 14 shows a flow chart of a robotic method in accordance with an example embodiment.

In accordance with an example embodiment, FIG. 14 shows a flow chart of a robotic method 1400 for a robotic system that includes a first manipulator arm 500 and a second manipulator arm 500', each manipulator arm including a movable distal portion, a proximal portion coupled to an associated base, and a plurality of joints between the distal portion and the base, the plurality of joints having a joint space with sufficient degrees of freedom to allow a range of differing joint states of the plurality of joints for a given state of the distal portion of each manipulator arm. A first operation 1402 includes determining a first reference geometry 700 of the first manipulator arm 500 and a second reference geometry 700' of the second manipulator arm 500', the first and second reference geometries 700, 700' being movable with the associated manipulator arms within a workspace and having ranges of motion that overlap within the workspace. A second operation 1404 includes determining a relative state between the first reference geometry 700 and the second reference geometry 700' in the workspace and a desired avoidance vector. A third operation 1406 includes calculating an avoidance movement of one or more of the joints so as to maintain a separation between the first and second reference geometries 700, 700' in the workspace, the avoidance movement being based on the desired avoidance vector so that the avoidance movement is contained within a null-space of a Jacobian associated with the respective manipulator arm, A fourth operation 1408 includes driving the one or more joints according to the calculated avoidance movement.

FIG. 13 shows a block diagram of an example embodiment of the system. In response to a manipulation command input by a user to effect a desired tip state, the system uses the present joint position, such as may be determined using joint state sensors, to compute the appropriate Jacobian and hence $dq_{perp}/dt$ to effect the desired tip state. The present joint positions can also be used to determine a distance (d) between a reference geometry of each manipulator arm. In response to a determination that a distance (d) between the between reference geometries of a reference pair on interacting elements of adjacent arms is less than a critical distance ($d_{min}$), the system determines joints velocities $dq_{null}/dt$ that increase (d), which can then be combined with $dq_{perp}/dt$ to obtain dq/dt, according to which the joint(s) are driven to effect the desired tip state concurrently with avoiding arm-to-arm collisions.

While the example embodiments have been described in some detail for clarity of understanding and by way of example, a variety of adaptations, modifications, and changes will be obvious to those of skill in the art. Hence, the scope of the present invention is limited solely by the appended claims.

What is claimed is:

1. A robotic method for a robotic system that includes a first manipulator arm and a second manipulator arm, each manipulator arm including a movable distal portion, a proximal portion coupled to an associated base, and a plurality of joints between the distal portion and the base, the plurality of joints having a joint space with sufficient degrees of freedom to allow a range of differing joint states of the plurality of joints for a given state of the distal portion of each manipulator arm, and the method comprising:
   determining a first reference geometry of the first manipulator arm and a second reference geometry of the second manipulator arm, the first and second reference geometries being movable with the associated manipulator arms within a workspace and having ranges of motion that overlap within the workspace;
   determining a relative state between the first reference geometry and the second reference geometry in the workspace and a desired avoidance vector;
   calculating an avoidance movement of one or more joints of the pluralities of joints of the first and second manipulator arms so as to maintain a separation between the first and second reference geometries in the workspace, the avoidance movement being based on the desired avoidance vector so that the avoidance movement is contained within a null-space of a Jacobian associated with the respective manipulator arm; and
   driving the one or more joints of the pluralities of joints of the first and second manipulator arms according to the calculated avoidance movement.

2. The robotic method of claim 1, wherein the avoidance movement is calculated in response to the determined relative state when the relative state corresponds to a less than desired clearance between the first and second reference geometries, and the calculated avoidance movement along the desired avoidance vector corresponds to an increase in clearance.

3. The robotic method of claim 1, wherein the relative state is determined using three-dimensional coordinates corresponding to the workspace of the manipulator arms.

4. The robotic method of claim 2, wherein the avoidance movement calculation includes converting the desired avoidance vector between the workspace and the joint space of the manipulator arms.

5. The robotic method of claim 1, wherein calculating the avoidance movement comprises:
   determining nearest points between the first and second reference geometries;
   calculating an avoidance vector between the nearest points in the workspace of the manipulator arms, the calculated avoidance vector corresponding to the desired avoidance vector;
   transforming the calculated avoidance vector into a joint velocity space; and
   projecting the calculated avoidance vector transformed into the joint velocity space onto the null-space to obtain the avoidance movement.

6. The robotic method of claim 1, wherein calculating the avoidance movement comprises:
   calculating nearest points between the first and second reference geometries to determine one or more avoidance points on the manipulator arm;
   determining an avoidance vector between the nearest points in a workspace of the manipulator arms, the avoidance vector in the workspace corresponding to the desired avoidance vector;

transforming original null-space basis vectors of the manipulator arm into motion of the one or more avoidance points on the manipulator arm; and combining the transformed null-space basis vectors with the avoidance vector in the workspace into a coefficient for the original null-space basis vectors to obtain the avoidance movement.

7. The robotic method of claim 2, wherein the relative state is determined using joint sensor data from each of the first and second manipulator arms.

8. The robotic method of claim 2, wherein the first reference geometry includes a line segment corresponding to a structure of the first manipulator arm and the second reference geometry includes a line segment corresponding to a structure of the second manipulator arm.

9. The robotic method of claim 8, wherein each of the first and second reference geometries comprise a plurality of line segments each corresponding to a structure on the respective manipulator arm, and determining the relative state further comprises:

determining a line segment of the plurality of line segments of the first reference geometry nearest a line segment of the plurality of line segments of the second reference geometry, the nearest line segments corresponding to nearest structures of the first and second manipulator; and calculating the desired avoidance vector so as to extend through the nearest line segments.

10. The robotic method of claim 9, wherein determining the nearest line segment comprises calculating the nearest distance between the line segments of the first reference geometry and the second reference geometry.

11. The robotic method of claim 1, wherein calculating the avoidance movement comprises:

calculating a repulsion force between the first and second reference geometries sufficient to maintain the separation between the first and second reference geometries when applied in a direction of the desired avoidance vector, and calculating a movement of the one or more joints of the pluralities of joints of the first and second manipulator arms in response to the repulsion force applied on the first and second manipulator arms along the desired avoidance vector.

12. The robotic method of claim 1, wherein calculating the avoidance movement comprises:

calculating a repulsion commanded velocity between the first and second reference geometries sufficient to maintain the separation between the first and second reference geometries when applied in a direction of the desired avoidance vector, and calculating a movement of the one or more joints of the pluralities of joints of the first and second manipulator arms in response to the repulsion commanded velocity applied at line segments that correspond to structures of the first and second manipulator arms along the desired avoidance vector.

13. The robotic method of claim 11, wherein the repulsion force has a magnitude inversely related to a separation distance between the first and second reference geometries.

14. The robotic method of claim 12, wherein the repulsion commanded velocity has a magnitude inversely related to a separation distance between the first and second reference geometries.

15. The robotic method of claim 1, wherein the first and second manipulator arms have ranges of motion that overlap, and the relative state between the first and second manipulator arms is determined by using proximity sensors mounted on driven linkages of the first and second manipulator arms.

16. The robotic method of claim 1, wherein the relative state between manipulator arms is determined using sensed positional information received from at least one mechanical, optical, ultrasonic, capacitive, inductive, resistive, or joint sensor.

17. The robotic method of claim 1, wherein the avoidance movement is independent of a planar relationship between the first and second manipulator arms when each arm is disposed in a substantially planar configuration, the avoidance movement allowing for an increased range of configurations for each arm while inhibiting collisions between the first and second manipulator arms where their respective ranges of motion overlap.

18. The robotic method of claim 1, wherein determining the relative state between the first and second reference geometries comprises any or all of a relative position, relative velocity and relative acceleration between the first and second reference geometries.

19. The robotic method of claim 1, wherein the distal portion of each arm comprises or is configured to releasably support a surgical instrument having an elongate shaft extending distally to a surgical end effector, wherein each instrument shaft pivots about a remote center during surgery, and wherein the avoidance movement of the one or more joints of the pluralities of joints of the first and second manipulator arms is calculated so as to maintain a position of the remote center during the driving of the one or more joints of the pluralities of joints of the first and second manipulator arms.

20. The robotic method of claim 19, further comprising:

receiving a manipulation command to move the end effector of one or both arms with a desired end effector movement;

calculating an end effector displacing movement of the joints of the respective arm to effect the desired end effector movement; and driving the joints according to the calculated end effector displacing movement, wherein calculating the end effector displacing movement of the joints further comprises calculating a movement of the joints within a null-perpendicular space of the Jacobian associated with the respective manipulator arm, the null-perpendicular space being orthogonal to the null-space.

21. The robotic method of claim 1, wherein the robotic system further includes one or more additional manipulator arms, the one or more additional manipulator arms having ranges of motion that overlap, each additional manipulator arm including a movable distal portion, a proximal portion coupled to the base, and a plurality of joints between the distal portion and the base, the plurality of joints having sufficient degrees of freedom to allow a range of differing joint states for a given state of its end effector, and the robotic method further comprises:

determining a reference geometry of each of the one or more additional manipulator arms, the reference geometry being movable with the associated additional manipulator arm within the workspace and having ranges of motion that overlap within the work space with that of the first or second manipulator arm; and determining a relative state between reference geometries having ranges of motion that overlap, wherein the avoidance movement is calculated so as to maintain a desired distance between the reference geometries of the one or more additional manipulator arms having ranges of motion that overlap.

22. The robotic method of claim 21, wherein calculating the avoidance movement comprises:
  determining a plurality of avoidance vectors corresponding to the desired avoidance vector, the plurality of avoidance vectors extending between any or all of the reference geometries having ranges of motion that overlap; and
  combining the plurality of avoidance vectors to obtain a resultant velocity vector for driving the one or more joints of the pluralities of joints of the first and second manipulator arms so as to simultaneously avoid a collision between the first and second manipulator arms while maintaining a desired state of the distal portion of each manipulator arm.

23. The robotic method of claim 20, wherein each manipulator arm is configured to support a tool having an intermediate portion with the intermediate portion extending along an insertion axis distally of the proximal portion and an end effector at a distal end of each intermediate portion, wherein at least some of the plurality of joints of that manipulator arm mechanically constrain a movement of the distal portion relative to the base such that the distal portion of the respective manipulator arm pivots about a remote center disposed extending through the insertion axis to facilitate a movement of the end effector at a work site, wherein the work site is accessed through an insertion opening.

24. The robotic method of claim 23, wherein the plurality of the joints of each manipulator arm comprises remote spherical center joints disposed distally of the proximal portion and proximally of the distal portion of the respective manipulator arm, wherein the remote spherical center joints are mechanically constrained so that articulation of the remote spherical center joints pivot the distal portion of the respective manipulator arm about first, second, and third remote center axes, the first, second, and third remote center axes intersecting its remote center.

25. The robotic method of claim 23, wherein the proximal portion of each manipulator arm is mechanically constrained relative to the base such that its distal portion pivots about its remote center when the proximal portion moves.

26. The robotic method of claim 23, wherein the the plurality of joints of each manipulator includes a revolute joint near a distal portion of that manipulator arm that pivots the insertion axis about an axis of the distal revolute joint, the axis extending through the remote center.

27. The robotic method of claim 26, wherein the end effector displacing movement is calculated so that the distal revolute joint is not driven.

28. The robotic method of claim 26, wherein the end effector displacing movement is calculated so that the distal revolute joint is not driven to effect a desired distal portion displacing movement.

29. The robotic method of claim 27, wherein the avoidance movement of the one or more joints of the pluralities of joints of the first and second manipulator arms is calculated so as to drive at least the distal revolute joint of one or more manipulator arms.

30. The robotic method of claim 23, wherein a first joint of the plurality of joints of each manipulator arm couples the proximal portion to the base, and an intermediate link is disposed proximal of and adjacent to the distal portion with a second joint therebetween, the second joint comprising a revolute joint mechanically constraining a movement of the distal portion relative to the intermediate link to rotation about a second joint axis, the second joint axis extending from the second joint distally toward the intermediate portion axis so as to intersect the insertion axis through the remote center.

31. The robotic method of claim 30, wherein the end effector displacing movement is calculated so that the second joint is not driven, and wherein the avoidance movement of the one or more joints of the pluralities of joints of the first and second manipulator arms is calculated to include driving of the second joint of one or more manipulator arms.

32. The robotic method of claim 30, wherein the end effector displacing movement is calculated so that the second joint is not driven to effect a desired distal portion displacing movement, and wherein the avoidance movement of the one or more joints of the pluralities of joints of the first and second manipulator arms is calculated to include driving of the second joint of one or more manipulator arms.

33. The robotic method of claim 23, wherein the first joint of each manipulator arm couples the proximal portion to the base, the first joint comprising a revolute joint that supports the distal portion of each manipulator arm such that a joint movement of the revolute joint pivots the distal portion of the respective manipulator arm about a pivotal axis of the revolute joint, wherein the pivotal axis extends from the revolute joint and through the respective remote center so that the insertion axis of the manipulator arm moves along a distally tapered cone oriented towards the remote center.

34. The robotic method of claim 33 further comprising:
  driving the first joint of the plurality of joints with a desired reconfiguration movement in response to a reconfiguration command;
  calculating a reconfiguration movement of one or more joints of the pluralities of joints of the first and second manipulator arms in response to the reconfiguration command so that the calculated reconfiguration movement of the first joint combined with the calculated avoidance movement is contained within a null-space of the Jacobian; and
  driving the one or more joints of the pluralities of joints of the first and second manipulator arms according to the calculated reconfiguration movement concurrently with driving one or more joints of the pluralities of joints of the first and second manipulator arms according to the calculated avoidance movement.

35. The robotic method of claim 34, wherein the first joint couples the proximal portion to the base so that the distal portion is moveable relative to the base along a path, the path being arcuate or substantially circular such that a movement of the proximal portion along the path pivots the insertion axis of the distal portion of the respective manipulator arm axis along a distally tapering cone oriented towards its remote center.

36. The robotic method of claim 35, wherein driving the first joint comprises moving the first joint along the path.

37. A robotic system comprising:
  a first and second manipulator arm, each arm having a distal portion and a proximal portion coupled to a proximal base and being configured for robotically moving the distal portion relative to the proximal base, each manipulator arm having a plurality of joints between the distal portion and the proximal base, the plurality of joints having a joint space with sufficient degrees of freedom to allow a range of joint states for a distal portion state of the first and second arms; and
  a processor configured to perform operations including:
    determining a first reference geometry of the first manipulator arm and a second reference geometry of the second manipulator arm, the first and second reference geometries movable with the associated manipulator arms within a workspace and having ranges of motion that overlap;

determining a relative state between the first reference geometry and the second reference geometry in the workspace;

determining a desired avoidance vector, calculating an avoidance movement of one or more joints of the pluralities of joints of the first and second manipulator arms to maintain a separation between the first and second reference geometries in the workspace, wherein the avoidance movement is calculated in the joint space, the avoidance movement being based on the desired avoidance vector so that the avoidance movement is contained within a null-space of a Jacobian associated with the respective manipulator arm; and driving the one or more joints of the pluralities of joints of the first and second manipulator arms according to the calculated avoidance movement.

38. The robotic system of claim 37, wherein the processor is further configured to calculate the avoidance movement in response to the determination of the relative state, when the relative state corresponds to a less than desired clearance between the first and second reference geometries and wherein the calculated movement along the desired avoidance vector corresponds to an increase in clearance.

39. The robotic system of claim 37, wherein the relative state is determined by the processor using three-dimensional coordinates corresponding to the workspace of the manipulator arms.

40. The robotic system of claim 37, wherein the avoidance movement calculation by the processor includes converting the desired avoidance vector between the workspace and the joint space of the manipulator arms.

41. The robotic system of claim 37, wherein each of the first and second manipulator arms comprise joint sensors, and wherein the determination of the relative state by the processor uses joint sensor data from the joint sensors of each of the first and second manipulator arms.

42. The robotic system of claim 37, wherein the first reference geometry includes a line segment corresponding to a structure of the first manipulator arm and the second reference geometry includes a segment corresponding to a structure of the second manipulator arm.

43. The robotic system of claim 42, wherein each of the first and second reference geometries comprise a plurality of line segments each corresponding to a structure on the respective manipulator arm, and determining the relative state further comprises:

determining a line segment of the plurality of line segments of the first reference geometry nearest a line segment of the plurality of line segments of the second reference geometry, the nearest line segments corresponding to nearest structures of the first and second manipulator; and calculating the desired avoidance vector so as to extend through the nearest line segments.

44. The robotic system of claim 41, wherein the processor is further configured so that calculating the avoidance movement comprises:

calculating a repulsion force between the first and second reference geometries sufficient to maintain a desired distance between the first and second reference geometries when applied in a direction of the desired avoidance vector, and calculating a movement of the one or more joints of the pluralities of joints of the first and second manipulator arms in response to the repulsion force applied on the manipulator arms along the desired avoidance vector.

45. The robotic system of claim 41, wherein the processor is further configured so that calculating the avoidance movement comprises:

calculating a repulsion commanded velocity between the first and second reference geometries sufficient to maintain a desired distance between the first and second reference geometries when applied in a direction of the desired avoidance vector, the first and second reference geometries including line segments for corresponding structures of the manipulator arms, and calculating a movement of the one or more joints of the pluralities of joints of the first and second manipulator arms in response to the repulsion commanded velocity applied on the line segments for the corresponding structures of the manipulator arms along the desired avoidance vector.

46. The robotic system of claim 44, wherein the repulsion force has a magnitude inversely related to the distance between the first and second reference geometries.

47. The robotic system of claim 45, wherein the repulsion commanded velocity has a magnitude inversely related to the distance between the first and second reference geometries.

48. The robotic system of claim 37, wherein determining the relative state between the first and second reference geometries comprises any or all of a relative position, relative velocity and relative acceleration between the first and second reference geometries.

49. The robotic system of claim 37 further comprising:

an input for receiving a manipulation command to move the distal portion with a desired distal portion movement, wherein the processor is further configured to perform operations including:

calculating a distal portion displacing movement of the plurality of joints in response to the manipulation command, wherein the distal portion displacing movement of the plurality of joints is calculated so that joint movement is contained within along a null-perpendicular space of the Jacobian, the null-perpendicular space being orthogonal to the null-space, and driving the pluralities of joints according to the calculated distal portion displacing movement of the plurality of joints so as to effect a desired distal portion movement.

50. The robotic system of claim 37, further comprising:

one or more additional manipulator arms, each arm including a movable distal portion, a proximal portion coupled to the base, and a plurality of joints between the distal portion and the base, the plurality of joints having a joint space with sufficient degrees of freedom to allow a range of differing joint states for a state of a distal portion of each of the one or more additional manipulator arms, wherein the processor is further configured to perform operations including:

determining a reference geometry on the one or more additional manipulator arms having a range of motion overlapping with the first or second reference geometries, determining a relative state between reference geometries having ranges of motion that overlap in the workspace and a desired avoidance vector between the reference geometry of the one or more additional manipulator arms and the first or second reference geometry, calculating the avoidance movement of one or more joints of the pluralities of joints of the one or more additional manipulator arms so as to maintain the separation between the reference geometries of each manipulator arm, wherein the avoidance movement is calculated in the joint space so that avoidance movement is contained within the null-space of the Jacobian, and driving the one or more joints of the pluralities of joints of the or more additional manipulator arms according to the calculated avoidance movement.

51. The robotic system of claim 37, wherein the distal portion of each arm comprises or is configured to releasably support a surgical instrument having an elongate shaft extending distally to a surgical end effector, wherein each instrument shaft pivots about a remote center during surgery, and wherein the avoidance movement of the one or more joints of the pluralities of joints of the first and second manipulator arms is calculated so as to maintain a position of the remote center during the driving of the pluralities of joints of the first and second manipulator arms.

52. The robotic system of claim 49, wherein each manipulator arm is configured to support a tool having an intermediate portion with the intermediate portion extending along an insertion axis distally of the proximal portion and an end effector at a distal end of each intermediate portion, wherein at least some of the plurality of joints of that manipulator arm mechanically constrain a movement of the distal portion relative to the base such that the distal portion of the respective manipulator arm pivots about a remote center disposed at the insertion axis to facilitate a movement of the end effector at a work site, wherein the work site is accessed through an insertion opening.

53. The robotic system of claim 52, wherein a plurality of the joints of each manipulator arm comprises remote spherical center joints disposed distally of the proximal portion and proximally of the distal portion of the respective manipulator arm, wherein the remote spherical center joints are mechanically constrained so that articulation of the remote spherical center joints pivot the distal portion of the respective manipulator arm about first, second, and third remote center axes, the first, second, and third remote center axes intersecting its remote center.

54. The robotic system of claim 52, wherein the proximal portion of each manipulator arm is mechanically constrained relative to the base such that its distal portion pivots about its remote center when the proximal portion moves.

55. The robotic system of claim 52, wherein the plurality of joints of each manipulator include a revolute joint near a distal portion of the manipulator arm that pivots the insertion axis about an axis of the distal revolute joint, the axis extending through the remote center.

56. The robotic system of claim 55, wherein the end effector displacing movement is calculated so that the distal revolute joint is not driven to effect the desired distal portion displacing movement.

57. The robotic system of claim 56, wherein the avoidance movement of the one or more joints of the pluralities of joints of the first and second manipulator arms is calculated so as to drive at least the distal revolute joint of one or more of the first and second manipulator arms.

58. The robotic system of claim 52, wherein a first joint couples the proximal portion to the base, and an intermediate link is disposed proximal of and adjacent to the distal portion with a second joint therebetween, the second joint comprising a revolute joint mechanically constraining a movement of the distal portion relative to the intermediate link to rotation about a second joint axis, the second joint axis extending from the second joint distally toward the intermediate portion axis so as to intersect the insertion axis extending through the remote center.

59. The robotic system of claim 58, wherein the end effector displacing movement is calculated so that the second joint is not driven to effect the desired distal portion displacing movement, and wherein the avoidance movement of the one or more joints of the pluralities of joints of the first and second manipulator arms is calculated to include driving the second joint of one or more manipulator arms.

60. The robotic system of claim 52, wherein a first joint of each manipulator arm couples the proximal portion to the base, the first joint comprising a revolute joint that supports the distal portion of each manipulator arm such that a joint movement of the revolute joint pivots the distal portion of the respective manipulator arm about a pivotal axis of the revolute joint, wherein the pivotal axis extends from the revolute joint and through the respective remote center so that the insertion axis of the manipulator arm moves along a distally tapered cone oriented towards the remote center.

61. The robotic system of claim 60 further comprising:
wherein the processor is further configured to calculate a reconfiguration movement of the pluralities of joints in response to a reconfiguration command so that the calculated avoidance movement of the one or more joints of the pluralities of joints of the first and second manipulator arms together with the calculated reconfiguration movement of the pluralities of joints of the first and second manipulator arms are within a null-space of a Jacobian associated with the first and second manipulator arms, the processor being configured to drive the pluralities of joints of the first and second manipulator arms according to the calculated reconfiguration movement during the calculated avoidance movement of the one or more joints of the first and second manipulator arms so as to maintain a desired state of the distal portion during the reconfiguration movement,
wherein the processor is configured to drive the pluralities of joints of the first and second manipulator arms according to the calculated reconfiguration movement concurrently with the calculated avoidance movement when the relative state corresponds to a separation between reference geometries of the first and second arms being less than desired so as to inhibit collisions between the first and second arms while effecting the desired reconfiguration movement.

62. The robotic system of claim 61, wherein the first joint couples the proximal portion to the base so that the distal portion is moveable relative to the base along a path, the path being arcuate or substantially circular such that a movement of the proximal portion along the path pivots the insertion axis of the distal portion of the respective manipulator arm axis along a distally tapering cone oriented towards its remote center.

63. The robotic system of claim 62, wherein the at least one joint is the first joint, and wherein driving of the at least one joint comprises translating the first joint along the path.

64. A robotic system comprising:
a first manipulator arm and a second manipulator arm, each manipulator arm including a distal end effector and being configured for robotically moving the distal end effector relative to a proximal base, each manipulator arm comprising a plurality of kinematically joined links, the plurality of links being moveable within a workspace and having sufficient degrees of freedom to allow a range of motion through a null-space of a Jacobian associated with the respective manipulator arm for a state of the end effector of the respective manipulator arm;
a processor coupled to the manipulator arms, the processor being configured to perform operations including:
  determining a first reference geometry of the first manipulator arm and a second reference geometry of the second manipulator arm, the first and second reference geometries having ranges of motion within the workspace that overlap,
  determining a relative state between the first reference geometry and the second reference geometry,
  calculating an avoidance movement of one or more links of the plurality of links of one or both of the first and second manipulators along an avoidance vector between the first and second reference geometries by driving one or more joints kinematically coupling the one or more links of the respective manipulator to maintain a separation between the first and second reference geometries, wherein the avoidance movement is calculated so that a movement of the one or more joints is within a null-space of the Jacobian, and
  moving the one or more links according to the calculated avoidance movement.

65. The robotic system of claim 64 further comprising:
an input for receiving a manipulation command to move each end effector with a desired end effector movement, the input being disposed on a user interface, wherein the processor is further configured to perform operations including:
  calculating an end effector displacing movement of the one or more links in response to the manipulation command, wherein calculating end effector displacing movement of the one or more links comprises calculating a movement of the one or more joints within a null-perpendicular-space of the Jacobian, the null-perpendicular-space being orthogonal to the null-space, and
  moving the one or more links according to the calculated end effector displacing movement of the one or more links by driving the one or more joints to effect the desired end effector movement.

66. The robotic system of claim 65, wherein the processor is further configured to calculate the avoidance movement so as to include driving of one or more joints that are not driven when calculating the end effector displacing movement.

* * * * *